United States Patent
Scheller

(10) Patent No.: US 10,597,669 B2
(45) Date of Patent: Mar. 24, 2020

(54) METHOD OF REDUCING ACETYLATION IN PLANTS TO IMPROVE BIOFUEL PRODUCTION

(71) Applicant: The Regents of the University of California, Oakland, CA (US)

(72) Inventor: Henrik Vibe Scheller, Millbrae, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/213,292

(22) Filed: Jul. 18, 2016

(65) Prior Publication Data

US 2017/0152522 A1 Jun. 1, 2017

Related U.S. Application Data

(63) Continuation of application No. 13/201,851, filed as application No. PCT/US2010/024477 on Feb. 17, 2010, now abandoned.

(60) Provisional application No. 61/153,202, filed on Feb. 17, 2009.

(51) Int. Cl.
*C12N 15/82* (2006.01)

(52) U.S. Cl.
CPC ..... *C12N 15/8246* (2013.01); *C12N 15/8242* (2013.01); *C12N 15/8243* (2013.01)

(58) Field of Classification Search
None
See application file for complete search history.

(56) References Cited

U.S. PATENT DOCUMENTS

| | | | | |
|---|---|---|---|---|
| 8,030,541 B2 * | 10/2011 | Davies | ............... | C07K 14/415 435/320.1 |
| 2003/0148318 A1 | 8/2003 | Jabon et al. | | |
| 2005/0125856 A1 | 6/2005 | Allen et al. | | |
| 2008/0124445 A1 | 5/2008 | Davies et al. | | |
| 2008/0213871 A1 | 9/2008 | Sticklen | | |
| 2008/0299613 A1 | 12/2008 | Merino et al. | | |

OTHER PUBLICATIONS

Manabe et al, 2011, Plant Physiology, 155:1068-1078.*
Thomas et al, 2001, Plant J., 25:417-425.*
Manabe et al, 2013, Plant Physiology, 163:1107-1117.*
Pawar et al, 2017, New Phytologist, 214:1491-1505.*
International Search Report dated Jun. 29, 2010, issued in related International Patent Application No. PCT/US2010/024477, filed Feb. 17, 2010.
International Preliminary Examination Report dated Aug. 23, 2011, issued in International Patent Application No. PCT/US2010/024477, filed Feb. 17, 2010.
Dhugga, "Plant Bgiomass Yield and Composition for Biofuels," 2007, Crop. Sci. vol. 47, pp. 2211-2227.
Gen Bank Accession No. NP_180988, O-Acetyltransferase family protein (*Arabidopsis thaliana*). Feb. 17, 2004.
Jabon et al., "Cas1p is a membrane protein necessary for the O-acetylation of the Cryptococcus neoformans capsular polysaccharide," 2001, Mol. Mlcrobiol, vol. 42, No. 2, pp. 453-467.
Lawford et al., "Performance testing of Zymomonas mobilis metabolically engineered for cofermentation of glucose, xylose, and arabinose," 2002, Appl. Biochem. Biotechnol., vol. 98-100, pp. 429-448.
Mannabe et al., "Loss-of Function Mutation of Reduced Wall Acetylation2 in Arabidopsis Leads to Reduced Cell Wall Acetylation and Increased Resistance to *Botrytis cinerea*," 2011, Plant Phys., vol. 155, pp. 1068-1078.
Scheller et al., "O-Acetylation of plant cell wall polysaccharides: identification and partial characterization of a rhamnogalacturonan O-acetyl-transferase from potato suspension-cultured cells," 2000, Planta, vol. 210, pp. 659-667.
Watanabe et al., "Comparative Genomics and Reverse Genetics Analysis Reveal Indispensable Functions of the Serine Acetyltransferase Gene Family in *Arabidopsis*," 2008, Plant Cell, vol. 20, No. 9, 2484-2496.
Waterhouse, et al., "Virus resistance and gene silencing in plants can be induced by simultaneous expression of sense and antisense RNA," 1998, PNAS, vol. 95, pp. 13959-13964.

* cited by examiner

*Primary Examiner* — Jason Deveau Rosen
(74) *Attorney, Agent, or Firm* — Kilpatrick Townsend & Stockton LLP

(57) ABSTRACT

The invention provides methods for engineering plants to have reduced levels of acetylation by decreasing expression of one or more Cas1L genes. Such plants can be used, e.g., to increase yield for biofuel production.

6 Claims, 6 Drawing Sheets

Specification includes a Sequence Listing.

Figure 1

```
CLUSTAL 2.0.7 multiple sequence alignment

P2_P._trichocarpa                   ------------------------------------------------
P3_P._trichocarpa                   ------------------------------------------------
Cas1L3_AT2G34410                    ----------------------MADSQPITPGQVSFLLGVIPVFIAW
Cas1L4_AT1G29890                    ------------------------------------------------
Cas1L1_AT5G46340                    ----------------------MVDPGPITPGQVSFLLGVIPIFVGW
Os01g0631100_Oryza                  ----------------------MEVFGPVTAGQVSFLLGLFPVLIAW
Os05g0582100_Oryza                  ----------------------MEVFGPVTPGQVSFLLGLFPVLIGW
Os03g0314200_Oryza                  ------------MAEAIASAGGIAMAASTSLTPGQVSALLGFLWVFTAW
Selaginella_estExt_Genewise1.C      ----------------------MVEISPPTTGQVALVLGFIPVLTAW
P1_P._trichocarpa                   MFAMLTGKKEEEGIGGPKEHWVDASMPMLSPVTPGQFSFLLGIVPVFAAW
P4_P._trichocarpa                   ------------------------------------------------
Cas1L2_AT3G06550                    ----------------------MASSSPVTPGLMSVVFGIVPVIVAW P2_P._trichocarpa                   -----------RSASAKFHSSAIKMNL----------------------
P3_P._trichocarpa                   --------LP-RSASAKFHSSATKMNL----------------------
Cas1L3_AT2G34410                    IYSEFLEYKR-SSLHSKVHSDNNLVELGEVKNKEDEGVVLLE-GGLPRSV
Cas1L4_AT1G29890                    ----------------MFSSHNIFLTIGIVFIR----------------
Cas1L1_AT5G46340                    IYSELLEYRK-SWVPLKPHSDNNLVELGDVAEKDDDKADLLE-GGLARSP
Os01g0631100_Oryza                  IYSEVLEYRK-SSSM-KVHSDSNLENGTVKEDD---KTVLLE-GGLSKSP
Os05g0582100_Oryza                  IYAEILEYRK-SLLYGKVHSDANLENETMKEDD---KAVLLE-GGQSKSP
Os03g0314200_Oryza                  AYAEVLYYRK-NAASIKAHSDVNLAVMDSSSNKGEDQVMLLE-EG-VQAP
Selaginella_estExt_Genewise1.C      LYSEFLEYRK-QPVPGKAHSDINLSELEHGPRRDNEKDSLLE-NGFSVSG
P1_P._trichocarpa                   IYTEYLEYKKNNTLAKA-HSDVGLVELGNEAVKEDDRAVLLE--GGVQSA
P4_P._trichocarpa                   ---------------------------------------------GLQPA
Cas1L2_AT3G06550                    LYSEYLHYAKYSVSAKTRHSDVNLVEIAKDFVKEDDKALLIEDGGGLQSA P2_P._trichocarpa                   -------------IRFMTLDDSFLLENRATLRAMSEFGAVLLYFYICDRT
P3_P._trichocarpa                   -------------IRFMTMDDSFLLENRTTLRVMSEFGAVLVYFYICDRT
Cas1L3_AT2G34410                    STKFYNSPIKTNLIRFLTLEDSFLIENRATLRAMAEFGAILFYFYISDRT
Cas1L4_AT1G29890                    -------------RFLTLEDSFLLENRATLRAMAEFGAILLYFYICDRT
Cas1L1_AT5G46340                    SVKFHNSSIRTNIIRFLSMEDSFLLEHRATLRAMSEFGAILIYFYICDRT
Os01g0631100_Oryza                  STKFRINSTKANLIRFITMDESFLLENRAVLRAMAEFGIVLVYFYICDRT
Os05g0582100_Oryza                  STKLRNMSTKANLIRFITMDESFLLENRAVLRAMAEVGIILVYFYICDRT
Os03g0314200_Oryza                  VQKPVYASLTSQMFRLFLLDQALILENRLTLRAISEFGGHLLYFYICDRT
Selaginella_estExt_Genewise1.C      TLKG-SFSIRMQLFKFFTLNETFLVENRSLLRAIAEFGCLLCYFYICDRT
P1_P._trichocarpa                   SPKARSSTSTFPIFRFFTMEEQFLIDNRLTLRAISEFGFFMVYFYICDRT
P4_P._trichocarpa                   SPKARTPTSSFPIFRFLMMEEQFLIDNRLTLRAILEFGFFMAYFYICDRT
Cas1L2_AT3G06550                    SPRAKGPTTHSPLIRFVLLDESFLVENRLTLRAIIEFAVLMVYFYICDRT
                                                 ::. ::: ::::::* **.: *..  : ****.***

P2_P._trichocarpa                   NILGESTKSYNRDLFVFLYILLIIVSSMTSLRKHTDKSAFTGKSMLYLNR
P3_P._trichocarpa                   NILGESTKNYNRDLFVFLYLLLIIVSAMTSLRKHTDKSTFTGKSTLYLNR
Cas1L3_AT2G34410                    SLLGESKKNYNRDLFLFLYCLLIIVSAMTSLKKHNDKSPITGKSILYLNR
Cas1L4_AT1G29890                    SLIGQSQKNYSRDLFLFLFCLLIIVSAMTSLKKHTDKSPITGKSILYLNR
Cas1L1_AT5G46340                    ELLGDSTKNYNRDLFLFLYVLLIIVSAMTSLRKHNDKSPISGKSILYLNR
Os01g0631100_Oryza                  NIFPESKKSYNRDLFLFLYILLIIASALTSLKKHHDKSAFSGKSILYLNR
Os05g0582100_Oryza                  NIFPETKKSYNRDLFLFLYILLIIASALTSLKKHNEKSAFTGKSILYLNR
Os03g0314200_Oryza                  NLLGESAKNYSRDMFLFLYFLLIIVAAMTSFKVHQDKSSFTGKSILYLNR
Selaginella_estExt_Genewise1.C      NVFGELKKNYSRDLFVFLYFLLIIVSSITSLKKHAEKSVASGKSILYLNR
P1_P._trichocarpa                   DILGSSKKSYNRDLFLFLYFLLIIVSAITSFKIHHDKSPFSGKPILYLNR
P4_P._trichocarpa                   DMLGSSKKSYNRDLFLFLYFLLIIVSAVTSFTIHHDKSPFSGKPILYLNR
Cas1L2_AT3G06550                    DVFNSSKKSYNRDLFLFLYFLLIIVSAITSFTIHTDKSPFSGKAIMYLNR
                                    .::  . *.*.**:*:**: ****.:::**:  * :** :**. :****
```

Figure 1-con't

```
P2_P._trichocarpa              HQTEEWKGWMQVLFLMYHYFAAAEIYNAIRIFIAAYVWMTGFGNFSYYYI
P3_P._trichocarpa              HQTEEWKGWMQVIFLMYHYFAATEIYNAIRVFIAAYVWMTGFGNFSYYYI
Cas1L3_AT2G34410               HQTEEWKGWMQVLFLMYHYFAAAEIYNAIRVFIAAYVWMTGFGNFSYYYI
Cas1L4_AT1G29890               HQTEEWKGWMQVLFLMYHYFAAVEFYNAIRVFIAGYVWMTGFGNFSYYYI
Cas1L1_AT5G46340               HQTEEWKGWMQVLFLMYHYFAAAEIYNAIRIFIAAYVWMTGFGNFSYYYV
Os01g0631100_Oryza             HQTEEWKGWMQVLFLMYHYFAATEIYNAIRVFIAAYVWMTGFGNFSYYYI
Os05g0582100_Oryza             HQTEEWKGWMQVLFLMYHYFAATEIYNAIRVFIAAYVWMTGFGNFSYYYI
Os03g0314200_Oryza             HQTEEWKGWMQVLFLMYHYFNAKEIYNAIRVFIAAYVWMTGFGNFSYYYV
Selaginella_estExt_Genewise1.C HQTEEWKGWMQVLFLMYHYFAAAEIYNAIRLFIAGYVWMTGFGNFSYYYV
P1_P._trichocarpa              HQTEEWKGWMQVLFLMYHYFAATEFYNAIRVFIASYVWMTGFGNFSYYYV
P4_P._trichocarpa              HQTEEWKGWMQVLFLMYHYFAATEIYNAIRMFIAAYVWMTGFGNFSYYYV
Cas1L2_AT3G06550               HQTEEWKGWMQVLFLMYHYFAAAEYYNAIRVFIACYVWMTGFGNFSYYYI
                               ************:****** * * *****:*** *************:

P2_P._trichocarpa              RKDFSVARFSQMMWRLNFFVAFCCIILNNDYMLYYICPMHTLFTLMVYGA
P3_P._trichocarpa              RKDFSVARFAQMMWRLNLFVAFCCIVLNNDYMLYYICPMHTLFTVMVYGV
Cas1L3_AT2G34410               RKDFSLARFTQMMWRLNLFVAFSCIILNNDYMLYYICPMHTLFTLMVYGA
Cas1L4_AT1G29890               RKDFSLARFTQMMWRLNFFVAFCCIILNNDYMLYYICPMHTLFTLMVYGA
Cas1L1_AT5G46340               RKDFSVARFAQMMWRLNFFVAFCCIVLNNDYMLYYICPMHTLFTLMVYGA
Os01g0631100_Oryza             KKDFSLARFAQMMWRLNFFVAFCCIVLDNDYMLYYICPMHTLFTLMVYGS
Os05g0582100_Oryza             KKDFSIARFAQMMWRLNFFVAFCCIVLDNDYMLYYICPMHTLFTLMVYGS
Os03g0314200_Oryza             RKDFSLARFAQMMWRLNFFVAFCCIVLNNDYTLYYICPMHTLFTLMVYGA
Selaginella_estExt_Genewise1.C RKDFSLGRFAQMMWRLNFLVTFCCIVLNNSYMLYYICPMHTLFTLMVYCS
P1_P._trichocarpa              RKDFSLARFAQMMWRLNFLVLVCCVVLNNSYMLYYICPMHTLFTLMVYAA
P4_P._trichocarpa              RKDFSLARFAQMMWRLNFLVLFCCVVLDNSYMLYYICPMHTLFTLMVYAA
Cas1L2_AT3G06550               RKDFSLARFAQMMWRLNFLVIFSCIVLNNSYMLYYICPMHTLFTLMVYGA
                               :****:.**:*******::*  ..*::*:*.* *************:***

P2_P._trichocarpa              LGIFNKYNENSSVMAVKILSCFLVVILIWEIPGVFDFLWSPLTFLLGYSD
P3_P._trichocarpa              LGIFNKYNENSSVIAVKILSCFLMVILIWETPGVFDILWSPLTFLLGYTD
Cas1L3_AT2G34410               LGIFSRYNEIPSVMALKIASCFLVVIVMWEIPGVFEIFWSPLTFLLGYTD
Cas1L4_AT1G29890               LGIYSQYNEIASVMALKIASCFLVVILMWEIPGVFEIFWSPLAFLLGYTD
Cas1L1_AT5G46340               LGIFSKYNEIGSVMALKIFSCFLVVFLLWEIPGAFEIFWGPLTFLLGYND
Os01g0631100_Oryza             LGLFNKYNEIPSVMAMKIVSCFLAVILIWEIPGVFELLWSPFTFLLGYKD
Os05g0582100_Oryza             LGLFNKYNEKPSVMAIKIACCFLTVILIWEIPGVFEFLWAPFTFLLGYKD
Os03g0314200_Oryza             LGILNKYNEIGSVMAIKFVACFLVVILIWEIPGVFEIVWSPFTFLLGYTD
Selaginella_estExt_Genewise1.C LGILNKYNEVPSVIGAKIAACFAVVILVWEVPGVFDFVWRPFTFLVEYTD
P1_P._trichocarpa              LGIFNKYNEIGSVMAAKIIACFLVVILMWEIPGVFEVVWSPFTFLFGYTD
P4_P._trichocarpa              LGIFNKYNEIGSVMAAKIIACFFVVILMWEIPGVFEVIWSPFTFLVGYTD
Cas1L2_AT3G06550               LGIMSKYNEMGSVIAAKFFACFVVVIIVWEIPGVFEWIWSPFTLLMGYND
                               **: .:***  **:. *: .**  *::** **.*: .* *:::*. *.*

P2_P._trichocarpa              P--AKPDLPRLHEWHFRSGLDRYIWIIGMIYAYFHPNIEKWMEKLEESET
P3_P._trichocarpa              P--AKPDLPRLHEWHFRSGLDRYIWIIGMIYAYFHPNVEKWMEKLEESEI
Cas1L3_AT2G34410               P--AKPELPLLHEWHFRSGLDRYIWIIGMIYAYFHPTVERWMEKLEECDA
Cas1L4_AT1G29890               P--AKPDLPRLHEWHFRSGLDRYIWIIGMIYAYFHPTVERWMEKLEECDA
Cas1L1_AT5G46340               P--AKPDLHRLHEWHFRSGLDRYIWIIGMIYAYYHPTVERWMEKLEDCET
Os01g0631100_Oryza             PEPSKANLPLLHEWHFRSGLDRYIWIIGMIYAYFHPNVERWMEKLEESET
Os05g0582100_Oryza             PEPSKANLPLLHEWHFRSGLDRYIWIIGMIYAYFHPNVERWMEKLEESET
Os03g0314200_Oryza             P--SKPDLPRLHEWHFRSGLDRYIWIVGMIYAYYHPTVEKWMEKLEEAET
Selaginella_estExt_Genewise1.C P--GKPDLPVLHEWHFRSGLDRYIWIYGMICAYFHPTVERWLEKLEELEC
P1_P._trichocarpa              P--AKPDLPRLHEWHFRSGLDRYIWIVGMIYAYYHPMVEGWMEKLEETEA
P4_P._trichocarpa              P--AKPDLPRLHEWHFRSGLDRYIWIIGMIYAYYHPKVEGWMEKLEETEA
Cas1L2_AT3G06550               P--AKPQLPLLHEWHFRSGLDRYIWIIGMLAYYHPTVESWMDKLEEAEM
                               *  .*.:*  **************** **: **:** :* *::**: :
```

Figure 1-con't

```
P2_P._trichocarpa              KKKLSMKTGIVAVSVSVGYLWYEYIYKLDKVS--YNKYHPYTSWIPITVY
P3_P._trichocarpa              KKKLSIKTGLVAVSLSVGYLWYECIYKLDKVS--YNKYHPYTSWIPITVY
Cas1L3_AT2G34410               KRKMSIKTSIIAISSFVGYLWYEYIYKLDKVT--YNKYHPYTSWIPITVY
Cas1L4_AT1G29890               KRRMSIKTSIIGISSFAGYLWYEYIYKLDKVT--YNKYHPYTSWIPITVY
Cas1L1_AT5G46340               KKRLSIKAAIVTITVLVGYVWYECIYKLDRTS--YNMYHPYTSWIPITVY
Os01g0631100_Oryza             KVRLSIKGTIISISLVAGYLWYEYIYKLDKIT--YNKYHPYTSWIPITVY
Os05g0582100_Oryza             KVRLFIKGAIVTLSLTAGYLWYEYIYRLDKIT--YNKYHPYTSWIPITVY
Os03g0314200_Oryza             KTKLYIKALIVSIALTAGCLWYEYIYKLDKIT--YNKYHPYTSWIPITVY
Selaginella_estExt_Genewise1.C RRKFTYKSVIVFVASLVGYLWYVHIYKLDKLS--YNKLHPYTSWIPISVY
P1_P._trichocarpa              KRRISIKTAVATISLAVGYMWYEYIYKLDKCVHLFEKCHPALPLLQLDPF
P4_P._trichocarpa              KRRIPIKTAVATISLAVGYTWYEYIYKLDKIS--YNKYHPYTSWIPITVY
Cas1L2_AT3G06550               KFRVAIKTSVALIALTVGYFWYEYIYKMDKLT--YNKYHPYTSWIPITVY
                               : :.  *  :  ::   .*  **  **::*:    ::  **  .  :  :  :

P2_P._trichocarpa              ICLRNCTQQLR-SFSSTLFAWLGKITLETYISQFHIWLRSDIPNGQPKWL
P3_P._trichocarpa              ICLRNCTQQLR-SFSLTLFAWLGKITLETYISQFHIWLRSDMPNGQPKWL
Cas1L3_AT2G34410               ICLRNSTQQLR-NFSMTLFAWLGKITLETYISQFHIWLRSNVPNGQPKWL
Cas1L4_AT1G29890               ICLRNCTQQLR-RFSLTLFAWLGKITLETYISQFHIWLRSSVPNGQPKLL
Cas1L1_AT5G46340               ICLRNFTHQLR-SVSLTLFAWLGKITLETYISQFHIWLRSNMPDGQPKWL
Os01g0631100_Oryza             ISLRNCTQQLR-NVSLTLFAWLGKITLETYISQIHIWLRSNMPDGQPKWL
Os05g0582100_Oryza             ICLRNCTQQLR-SASLALFAWLGKITLETYISQIHIWLRSSTPNGQPKWL
Os03g0314200_Oryza             ICLRNFTQEFR-CCSLTLFAWLGKITLETYISQFHIWLRSKVPNGQPKWL
Selaginella_estExt_Genewise1.C IVLRNVSQPLR-NWSLTLFAWLGKITLETYIAQFHIWLRTGVSNGQPKLL
P1_P._trichocarpa              RLNHLLEALIGGNLRELLFLWLGKITLETYISQIHIWLRSGIPDGQPKLL
P4_P._trichocarpa              ICLRNVTQQFR-CYSLTLFAWLGKITLETYISQIHIWLRSGIPDGQPKLL
Cas1L2_AT3G06550               ICLRNITQSFR-GYSLTLLAWLGKITLETYISQFHIWLRSGVPDGQPKLL
                                  :       :       *: **********:*:*****:  .:**** *

P2_P._trichocarpa              LSFIPEYPLLNFMLTTAIYVLVSHRLFELTNTLKTVFIPTKDNKRLFYNS
P3_P._trichocarpa              LSVIPEYPLLNFMLTTAIYVLVSHRLFELTNTLKTVFIPTKDNMRLFYNF
Cas1L3_AT2G34410               LCIIPEYPMLNFMLVTAIYVLVSHRLFELTNTLKSVFIPTKDDKRLLHNV
Cas1L4_AT1G29890               LSIIPEYPMLNFMLTTAIYVLVSVRLFELTNTLKSVFIPTKDDKRLLHNV
Cas1L1_AT5G46340               LSIIPGYPMLNFMLTTAIYVLVSHRLFELTNTLKTVFVPTKDNKRLFSNF
Os01g0631100_Oryza             LSFIPGYPLLNFMLATAIYLLISYRVFELTGVLKSAFIPSRDNNRLYQNF
Os05g0582100_Oryza             LSFVPDYPLLNFMLTTAIYLLLSYRVFEITGVLKGAFIPSRDNNRLYQNF
Os03g0314200_Oryza             LTIIPNYPMLNFMLTTAIYVAVSHRLFELTNTLKIAFVPSRDNKRLSYNF
Selaginella_estExt_Genewise1.C LSFIPDYPMLNFMLATSIYILVSYRLFELTNTLKSAFVPNKDNNRLFLMV
P1_P._trichocarpa              LSLIPDYPMLNFMLTTSIYVAVSYRLFDLTNTLKTAFVPSKDDKRLTNNI
P4_P._trichocarpa              LSLIPDYPMLNFMLTTSIYIGVSYRLFDLTNTLKTAFVPSKDNKRLTNNI
Cas1L2_AT3G06550               LSLVPDYPLLNFMLTTSIYVAISYRLFELTNTLKTAFIPTKDDKRLVYNT
                               *  .:* **:*****.*:**:  :*  *:*::*..**  .*:*.:*:  **

P2_P._trichocarpa              VAGAAISVCLYCVAVILLHIPHSPA---------------------
P3_P._trichocarpa              VAGAAISLCLYCVAVILLHILHSAVSPSLVLENNMVASDDLELCS---
Cas1L3_AT2G34410               LAGAAISFCLYLTSLILLQIPH------------------------
Cas1L4_AT1G29890               IAMAAISFCLYIIGLILLLIPH------------------------
Cas1L1_AT5G46340               IAGIAIALPLYCFSFVLLQIHR------------------------
Os01g0631100_Oryza             VAGIAISVCLYFLSIVLLKIPIV-----------------------
Os05g0582100_Oryza             IAGIAISACLYFCSLILVKITIV-----------------------
Os03g0314200_Oryza             VAGIAISVALYSLSFLIVGVAGY-----------------------
Selaginella_estExt_Genewise1.C VSGGTIFSLLYGVSYLLVKFAPQMLVLTIRTD---------------
P1_P._trichocarpa              ITAVAVSIVLYSLSFVFLKAPQMLVLTIRTD----------------
P4_P._trichocarpa              ITAAAVSSVLYSLSFVFLKVPQMLINDNLCAVCHLNAQFADTLNLQV-
Cas1L2_AT3G06550               ISALIICTCLYFFSFILITIPQKLVSQNFIFLCGRKLFFPWYLSSLIC
                               ::    :   **   .  :::
```

Acetate content is expressed in arbitrary units.

|     | % of WT | p (t-test, statistically significance of difference to WT) |
| --- | --- | --- |
| L1  | 99.8 | 0.97 |
| L2  | 77.6 | 0.0014 |
| L3  | 92.1 | 0.28 |
| L4  | 90.0 | 0.13 |
| WT  | 100 |  | ized. Efficient biofuel production requires efficient degradation of these polysaccharides. Enzymatic degradation into monosaccharides is hindered, however, by acetyl ester substitutions on the polysaccharide backbone. The inhibition of degradation by acetyl esters can be significant, as substitution can be at a high level, e.g., typically 25-50% of the xylose residues of grass xylans are acetylated. Moreover, the acetic acid that is released during enzymatic or chemical degradation is inhibitory to organisms, such as yeast, that are used for fermentation. The acetic acid contained in a biomass mixture for fermentation can easily be in the order of 0.1 M or 6 g/l, which is a highly inhibitory level. Reduction in the level of acetic acid would therefore be highly beneficial for fermentation. Accordingly, there is a need for improvement to biofuel production to reduce acetic acid levels.

SEQUENCE LISTING

<160> NUMBER OF SEQ ID NOS: 22

<210> SEQ ID NO 1
<211> LENGTH: 540
<212> TYPE: PRT
<213> ORGANISM: Arabidopsis thaliana
<220> FEATURE:
<223> OTHER INFORMATION: CAS1L1 Arabidopsis sequence (NP_568662.1, AT5G46340)

<400> SEQUENCE: 1

```
Met Val Asp Pro Gly Pro Ile Thr Pro Gly Gln Val Ser Phe Leu Leu
1               5                   10                  15

Gly Val Ile Pro Ile Phe Val Gly Trp Ile Tyr Ser Glu Leu Leu Glu
            20                  25                  30

Tyr Arg Lys Ser Trp Val Pro Leu Lys Pro His Ser Asp Asn Asn Leu
        35                  40                  45

Val Glu Leu Gly Asp Val Ala Glu Lys Asp Asp Lys Ala Asp Leu
    50                  55                  60

Leu Glu Gly Gly Leu Ala Arg Ser Pro Ser Val Lys Phe His Asn Ser
65                  70                  75                  80

Ser Ile Arg Thr Asn Ile Ile Arg Phe Leu Ser Met Glu Asp Ser Phe
                85                  90                  95

Leu Leu Glu His Arg Ala Thr Leu Arg Ala Met Ser Glu Phe Gly Ala
            100                 105                 110

Ile Leu Ile Tyr Phe Tyr Ile Cys Asp Arg Thr Glu Leu Leu Gly Asp
        115                 120                 125

Ser Thr Lys Asn Tyr Asn Arg Asp Leu Phe Leu Phe Leu Tyr Val Leu
    130                 135                 140

Leu Ile Ile Val Ser Ala Met Thr Ser Leu Arg Lys His Asn Asp Lys
145                 150                 155                 160

Ser Pro Ile Ser Gly Lys Ser Ile Leu Tyr Leu Asn Arg His Gln Thr
                165                 170                 175

Glu Glu Trp Lys Gly Trp Met Gln Val Leu Phe Leu Met Tyr His Tyr
            180                 185                 190

Phe Ala Ala Ala Glu Ile Tyr Asn Ala Ile Arg Ile Phe Ile Ala Ala
        195                 200                 205

Tyr Val Trp Met Thr Gly Phe Gly Asn Phe Ser Tyr Tyr Tyr Val Arg
    210                 215                 220

Lys Asp Phe Ser Val Ala Arg Phe Ala Gln Met Met Trp Arg Leu Asn
225                 230                 235                 240

Phe Phe Val Ala Phe Cys Cys Ile Val Leu Asn Asn Asp Tyr Met Leu
                245                 250                 255

Tyr Tyr Ile Cys Pro Met His Thr Leu Phe Thr Leu Met Val Tyr Gly
            260                 265                 270

Ala Leu Gly Ile Phe Ser Lys Tyr Asn Glu Ile Gly Ser Val Met Ala
        275                 280                 285

Leu Lys Ile Phe Ser Cys Phe Leu Val Val Phe Leu Leu Trp Glu Ile
    290                 295                 300

Pro Gly Ala Phe Glu Ile Phe Trp Gly Pro Leu Thr Phe Leu Leu Gly
```

```
305                 310                 315                 320
Tyr Asn Asp Pro Ala Lys Pro Asp Leu His Arg Leu His Glu Trp His
                325                 330                 335
Phe Arg Ser Gly Leu Asp Arg Tyr Ile Trp Ile Ile Gly Met Ile Tyr
                340                 345                 350
Ala Tyr Tyr His Pro Thr Val Glu Arg Trp Met Glu Lys Leu Glu Asp
                355                 360                 365
Cys Glu Thr Lys Lys Arg Leu Ser Ile Lys Ala Ala Ile Val Thr Ile
                370                 375                 380
Thr Val Leu Val Gly Tyr Val Trp Tyr Glu Cys Ile Tyr Lys Leu Asp
385                 390                 395                 400
Arg Thr Ser Tyr Asn Met Tyr His Pro Tyr Thr Ser Trp Ile Pro Ile
                405                 410                 415
Thr Val Tyr Ile Cys Leu Arg Asn Phe Thr His Gln Leu Arg Ser Val
                420                 425                 430
Ser Leu Thr Leu Phe Ala Trp Leu Gly Lys Ile Thr Leu Glu Thr Tyr
                435                 440                 445
Ile Ser Gln Phe His Ile Trp Leu Arg Ser Asn Met Pro Asp Gly Gln
                450                 455                 460
Pro Lys Trp Leu Leu Ser Ile Ile Pro Gly Tyr Pro Met Leu Asn Phe
465                 470                 475                 480
Met Leu Thr Thr Ala Ile Tyr Val Leu Val Ser His Arg Leu Phe Glu
                485                 490                 495
Leu Thr Asn Thr Leu Lys Thr Val Phe Val Pro Thr Lys Asp Asn Lys
                500                 505                 510
Arg Leu Phe Ser Asn Phe Ile Ala Gly Ile Ala Ile Ala Leu Pro Leu
                515                 520                 525
Tyr Cys Phe Ser Phe Val Leu Leu Gln Ile His Arg
                530                 535                 540

<210> SEQ ID NO 2
<211> LENGTH: 544
<212> TYPE: PRT
<213> ORGANISM: Arabidopsis thaliana
<220> FEATURE:
<223> OTHER INFORMATION: Cas1L2 protein sequence (NP_001118592.1,
      AT3G06550)

<400> SEQUENCE: 2

Met Ala Ser Ser Ser Pro Val Thr Pro Gly Leu Met Ser Val Val Phe
1               5                   10                  15
Gly Ile Val Pro Val Ile Val Ala Trp Leu Tyr Ser Glu Tyr Leu His
                20                  25                  30
Tyr Ala Lys Tyr Ser Val Ser Ala Lys Thr His Ser Asp Val Asn Leu
                35                  40                  45
Val Glu Ile Ala Lys Asp Phe Val Lys Glu Asp Lys Ala Leu Leu
                50                  55                  60
Ile Glu Asp Gly Gly Leu Gln Ser Ala Ser Pro Arg Ala Lys Gly
65                  70                  75                  80
Pro Thr Thr His Ser Pro Leu Ile Arg Phe Val Leu Leu Asp Glu Ser
                85                  90                  95
Phe Leu Val Glu Asn Arg Leu Thr Leu Arg Ala Ile Ile Glu Phe Ala
                100                 105                 110
Val Leu Met Val Tyr Phe Tyr Ile Cys Asp Arg Thr Asp Val Phe Asn
                115                 120                 125
```

```
Ser Ser Lys Lys Ser Tyr Asn Arg Asp Leu Phe Leu Phe Tyr Phe
    130                 135                 140

Leu Leu Ile Ile Val Ser Ala Ile Thr Ser Phe Thr Ile His Thr Asp
145                 150                 155                 160

Lys Ser Pro Phe Ser Gly Lys Ala Ile Met Tyr Leu Asn Arg His Gln
                165                 170                 175

Thr Glu Glu Trp Lys Gly Trp Met Gln Val Leu Phe Leu Met Tyr His
                180                 185                 190

Tyr Phe Ala Ala Ala Glu Tyr Tyr Asn Ala Ile Arg Val Phe Ile Ala
                195                 200                 205

Cys Tyr Val Trp Met Thr Gly Phe Gly Asn Phe Ser Tyr Tyr Tyr Ile
    210                 215                 220

Arg Lys Asp Phe Ser Leu Ala Arg Phe Ala Gln Met Met Trp Arg Leu
225                 230                 235                 240

Asn Phe Leu Val Ile Phe Ser Cys Ile Val Leu Asn Asn Ser Tyr Met
                245                 250                 255

Leu Tyr Tyr Ile Cys Pro Met His Thr Leu Phe Thr Leu Met Val Tyr
                260                 265                 270

Gly Ala Leu Gly Ile Met Ser Lys Tyr Asn Glu Met Gly Ser Val Ile
    275                 280                 285

Ala Ala Lys Phe Phe Ala Cys Phe Val Val Ile Ile Val Trp Glu
290                 295                 300

Ile Pro Gly Val Phe Glu Trp Ile Trp Ser Pro Phe Thr Leu Leu Met
305                 310                 315                 320

Gly Tyr Asn Asp Pro Ala Lys Pro Gln Leu Pro Leu Leu His Glu Trp
                325                 330                 335

His Phe Arg Ser Gly Leu Asp Arg Tyr Ile Trp Ile Ile Gly Met Leu
            340                 345                 350

Tyr Ala Tyr Tyr His Pro Thr Val Glu Ser Trp Met Asp Lys Leu Glu
        355                 360                 365

Glu Ala Glu Met Lys Phe Arg Val Ala Ile Lys Thr Ser Val Ala Leu
    370                 375                 380

Ile Ala Leu Thr Val Gly Tyr Phe Trp Tyr Glu Tyr Ile Tyr Lys Met
385                 390                 395                 400

Asp Lys Leu Thr Tyr Asn Lys Tyr His Pro Tyr Thr Ser Trp Ile Pro
                405                 410                 415

Ile Thr Val Tyr Ile Cys Leu Arg Asn Ile Thr Gln Ser Phe Arg Gly
            420                 425                 430

Tyr Ser Leu Thr Leu Leu Ala Trp Leu Gly Lys Ile Thr Leu Glu Thr
        435                 440                 445

Tyr Ile Ser Gln Phe His Ile Trp Leu Arg Ser Gly Val Pro Asp Gly
    450                 455                 460

Gln Pro Lys Leu Leu Leu Ser Leu Val Pro Asp Tyr Pro Leu Leu Asn
465                 470                 475                 480

Phe Met Leu Thr Thr Ser Ile Tyr Val Ala Ile Ser Tyr Arg Leu Phe
                485                 490                 495

Glu Leu Thr Asn Thr Leu Lys Thr Ala Phe Ile Pro Thr Lys Asp Asp
                500                 505                 510

Lys Arg Leu Val Tyr Asn Thr Ile Ser Ala Leu Ile Ile Cys Thr Cys
            515                 520                 525

Leu Tyr Phe Phe Ser Phe Ile Leu Ile Thr Ile Pro Gln Lys Leu Val
    530                 535                 540
```

-continued

```
<210> SEQ ID NO 3
<211> LENGTH: 540
<212> TYPE: PRT
<213> ORGANISM: Arabidopsis thaliana
<220> FEATURE:
<223> OTHER INFORMATION: Cas1L3 protein sequence (NP_001031478.1,
      AT2G34410)

<400> SEQUENCE: 3

Met Ala Asp Ser Gln Pro Ile Thr Pro Gly Gln Val Ser Phe Leu Leu
1               5                   10                  15

Gly Val Ile Pro Val Phe Ile Ala Trp Ile Tyr Ser Glu Phe Leu Glu
            20                  25                  30

Tyr Lys Arg Ser Ser Leu His Ser Lys Val His Ser Asp Asn Asn Leu
        35                  40                  45

Val Glu Leu Gly Glu Val Lys Asn Lys Glu Asp Glu Gly Val Val Leu
    50                  55                  60

Leu Glu Gly Gly Leu Pro Arg Ser Val Ser Thr Lys Phe Tyr Asn Ser
65                  70                  75                  80

Pro Ile Lys Thr Asn Leu Ile Arg Phe Leu Thr Leu Glu Asp Ser Phe
                85                  90                  95

Leu Ile Glu Asn Arg Ala Thr Leu Arg Ala Met Ala Glu Phe Gly Ala
            100                 105                 110

Ile Leu Phe Tyr Phe Tyr Ile Ser Asp Arg Thr Ser Leu Leu Gly Glu
        115                 120                 125

Ser Lys Lys Asn Tyr Asn Arg Asp Leu Phe Leu Phe Leu Tyr Cys Leu
    130                 135                 140

Leu Ile Ile Val Ser Ala Met Thr Ser Leu Lys Lys His Asn Asp Lys
145                 150                 155                 160

Ser Pro Ile Thr Gly Lys Ser Ile Leu Tyr Leu Asn Arg His Gln Thr
                165                 170                 175

Glu Glu Trp Lys Gly Trp Met Gln Val Leu Phe Leu Met Tyr His Tyr
            180                 185                 190

Phe Ala Ala Ala Glu Ile Tyr Asn Ala Ile Arg Val Phe Ile Ala Ala
        195                 200                 205

Tyr Val Trp Met Thr Gly Phe Gly Asn Phe Ser Tyr Tyr Tyr Ile Arg
    210                 215                 220

Lys Asp Phe Ser Leu Ala Arg Phe Thr Gln Met Met Trp Arg Leu Asn
225                 230                 235                 240

Leu Phe Val Ala Phe Ser Cys Ile Ile Leu Asn Asn Asp Tyr Met Leu
                245                 250                 255

Tyr Tyr Ile Cys Pro Met His Thr Leu Phe Thr Leu Met Val Tyr Gly
            260                 265                 270

Ala Leu Gly Ile Phe Ser Arg Tyr Asn Glu Ile Pro Ser Val Met Ala
        275                 280                 285

Leu Lys Ile Ala Ser Cys Phe Leu Val Val Ile Val Met Trp Glu Ile
    290                 295                 300

Pro Gly Val Phe Glu Ile Phe Trp Ser Pro Leu Thr Phe Leu Leu Gly
305                 310                 315                 320

Tyr Thr Asp Pro Ala Lys Pro Glu Leu Pro Leu Leu His Glu Trp His
                325                 330                 335

Phe Arg Ser Gly Leu Asp Arg Tyr Ile Trp Ile Ile Gly Met Ile Tyr
            340                 345                 350

Ala Tyr Phe His Pro Thr Val Glu Arg Trp Met Glu Lys Leu Glu Glu
        355                 360                 365
```

```
Cys Asp Ala Lys Arg Lys Met Ser Ile Lys Thr Ser Ile Ile Ala Ile
    370                 375                 380

Ser Ser Phe Val Gly Tyr Leu Trp Tyr Glu Tyr Ile Tyr Lys Leu Asp
385                 390                 395                 400

Lys Val Thr Tyr Asn Lys Tyr His Pro Tyr Thr Ser Trp Ile Pro Ile
                405                 410                 415

Thr Val Tyr Ile Cys Leu Arg Asn Ser Thr Gln Gln Leu Arg Asn Phe
                420                 425                 430

Ser Met Thr Leu Phe Ala Trp Leu Gly Lys Ile Thr Leu Glu Thr Tyr
            435                 440                 445

Ile Ser Gln Phe His Ile Trp Leu Arg Ser Asn Val Pro Asn Gly Gln
        450                 455                 460

Pro Lys Trp Leu Leu Cys Ile Ile Pro Glu Tyr Pro Met Leu Asn Phe
465                 470                 475                 480

Met Leu Val Thr Ala Ile Tyr Val Leu Val Ser His Arg Leu Phe Glu
                485                 490                 495

Leu Thr Asn Thr Leu Lys Ser Val Phe Ile Pro Thr Lys Asp Asp Lys
                500                 505                 510

Arg Leu Leu His Asn Val Leu Ala Gly Ala Ala Ile Ser Phe Cys Leu
            515                 520                 525

Tyr Leu Thr Ser Leu Ile Leu Leu Gln Ile Pro His
    530                 535                 540

<210> SEQ ID NO 4
<211> LENGTH: 470
<212> TYPE: PRT
<213> ORGANISM: Arabidopsis thaliana
<220> FEATURE:
<223> OTHER INFORMATION: Cas1L4 protein sequence (NP174282.2, AT1G29890)

<400> SEQUENCE: 4

Met Phe Ser Ser His Asn Ile Phe Leu Thr Ile Gly Ile Val Phe Ile
1               5                   10                  15

Arg Arg Phe Leu Thr Leu Glu Asp Ser Phe Leu Leu Glu Asn Arg Ala
                20                  25                  30

Thr Leu Arg Ala Met Ala Glu Phe Gly Ala Ile Leu Leu Tyr Phe Tyr
            35                  40                  45

Ile Cys Asp Arg Thr Ser Leu Ile Gly Gln Ser Gln Lys Asn Tyr Ser
50                  55                  60

Arg Asp Leu Phe Leu Phe Leu Phe Cys Leu Leu Ile Ile Val Ser Ala
65                  70                  75                  80

Met Thr Ser Leu Lys Lys His Thr Asp Lys Ser Pro Ile Thr Gly Lys
                85                  90                  95

Ser Ile Leu Tyr Leu Asn Arg His Gln Thr Glu Glu Trp Lys Gly Trp
                100                 105                 110

Met Gln Val Leu Phe Leu Met Tyr His Tyr Phe Ala Ala Val Glu Phe
            115                 120                 125

Tyr Asn Ala Ile Arg Val Phe Ile Ala Gly Tyr Val Trp Met Thr Gly
        130                 135                 140

Phe Gly Asn Phe Ser Tyr Tyr Tyr Ile Arg Lys Asp Phe Ser Leu Ala
145                 150                 155                 160

Arg Phe Thr Gln Met Met Trp Arg Leu Asn Phe Phe Val Ala Phe Cys
                165                 170                 175

Cys Ile Ile Leu Asn Asn Asp Tyr Met Leu Tyr Tyr Ile Cys Pro Met
                180                 185                 190
```

```
His Thr Leu Phe Thr Leu Met Val Tyr Gly Ala Leu Gly Ile Tyr Ser
            195                 200                 205

Gln Tyr Asn Glu Ile Ala Ser Val Met Ala Leu Lys Ile Ala Ser Cys
    210                 215                 220

Phe Leu Val Val Ile Leu Met Trp Glu Ile Pro Gly Val Phe Glu Ile
225                 230                 235                 240

Phe Trp Ser Pro Leu Ala Phe Leu Leu Gly Tyr Thr Asp Pro Ala Lys
                245                 250                 255

Pro Asp Leu Pro Arg Leu His Glu Trp His Phe Arg Ser Gly Leu Asp
            260                 265                 270

Arg Tyr Ile Trp Ile Ile Gly Met Ile Tyr Ala Tyr Phe His Pro Thr
    275                 280                 285

Val Glu Arg Trp Met Glu Lys Leu Glu Glu Cys Asp Ala Lys Arg Arg
290                 295                 300

Met Ser Ile Lys Thr Ser Ile Ile Gly Ile Ser Ser Phe Ala Gly Tyr
305                 310                 315                 320

Leu Trp Tyr Glu Tyr Ile Tyr Lys Leu Asp Lys Val Thr Tyr Asn Lys
                325                 330                 335

Tyr His Pro Tyr Thr Ser Trp Ile Pro Ile Thr Val Tyr Ile Cys Leu
            340                 345                 350

Arg Asn Cys Thr Gln Gln Leu Arg Arg Phe Ser Leu Thr Leu Phe Ala
    355                 360                 365

Trp Leu Gly Lys Ile Thr Leu Glu Thr Tyr Ile Ser Gln Phe His Ile
            370                 375                 380

Trp Leu Arg Ser Ser Val Pro Asn Gly Gln Pro Lys Leu Leu Leu Ser
385                 390                 395                 400

Ile Ile Pro Glu Tyr Pro Met Leu Asn Phe Met Leu Thr Thr Ala Ile
                405                 410                 415

Tyr Val Leu Val Ser Val Arg Leu Phe Glu Leu Thr Asn Thr Leu Lys
            420                 425                 430

Ser Val Phe Ile Pro Thr Lys Asp Asp Lys Arg Leu Leu His Asn Val
    435                 440                 445

Ile Ala Met Ala Ala Ile Ser Phe Cys Leu Tyr Ile Ile Gly Leu Ile
450                 455                 460

Leu Leu Leu Ile Pro His
465                 470

<210> SEQ ID NO 5
<211> LENGTH: 568
<212> TYPE: PRT
<213> ORGANISM: Arabidopsis thaliana
<220> FEATURE:
<223> OTHER INFORMATION: Cas1L2 protein sequence (NP_001078116.1,
      AT3G06550)

<400> SEQUENCE: 5

Met Ala Ser Ser Ser Pro Val Thr Pro Gly Leu Met Ser Val Val Phe
1               5                   10                  15

Gly Ile Val Pro Val Ile Val Ala Trp Leu Tyr Ser Glu Tyr Leu His
            20                  25                  30

Tyr Ala Lys Tyr Ser Val Ser Ala Lys Thr Arg His Ser Asp Val Asn
        35                  40                  45

Leu Val Glu Ile Ala Lys Asp Phe Val Lys Glu Asp Lys Ala Leu
    50                  55                  60

Leu Ile Glu Asp Gly Gly Gly Leu Gln Ser Ala Ser Pro Arg Ala Lys
65                  70                  75                  80
```

```
Gly Pro Thr Thr His Ser Pro Leu Ile Arg Phe Val Leu Leu Asp Glu
                85                  90                  95

Ser Phe Leu Val Glu Asn Arg Leu Thr Leu Arg Ala Ile Ile Glu Phe
            100                 105                 110

Ala Val Leu Met Val Tyr Phe Tyr Ile Cys Asp Arg Thr Asp Val Phe
        115                 120                 125

Asn Ser Ser Lys Lys Ser Tyr Asn Arg Asp Leu Phe Leu Phe Leu Tyr
    130                 135                 140

Phe Leu Leu Ile Ile Val Ser Ala Ile Thr Ser Phe Thr Ile His Thr
145                 150                 155                 160

Asp Lys Ser Pro Phe Ser Gly Lys Ala Ile Met Tyr Leu Asn Arg His
                165                 170                 175

Gln Thr Glu Glu Trp Lys Gly Trp Met Gln Val Leu Phe Leu Met Tyr
            180                 185                 190

His Tyr Phe Ala Ala Ala Glu Tyr Tyr Asn Ala Ile Arg Val Phe Ile
        195                 200                 205

Ala Cys Tyr Val Trp Met Thr Gly Phe Gly Asn Phe Ser Tyr Tyr Tyr
    210                 215                 220

Ile Arg Lys Asp Phe Ser Leu Ala Arg Phe Ala Gln Met Met Trp Arg
225                 230                 235                 240

Leu Asn Phe Leu Val Ile Phe Ser Cys Ile Val Leu Asn Asn Ser Tyr
                245                 250                 255

Met Leu Tyr Tyr Ile Cys Pro Met His Thr Leu Phe Thr Leu Met Val
            260                 265                 270

Tyr Gly Ala Leu Gly Ile Met Ser Lys Tyr Asn Glu Met Gly Ser Val
        275                 280                 285

Ile Ala Ala Lys Phe Phe Ala Cys Phe Val Val Ile Ile Val Trp
    290                 295                 300

Glu Ile Pro Gly Val Phe Glu Trp Ile Trp Ser Pro Phe Thr Leu Leu
305                 310                 315                 320

Met Gly Tyr Asn Asp Pro Ala Lys Pro Gln Leu Pro Leu Leu His Glu
                325                 330                 335

Trp His Phe Arg Ser Gly Leu Asp Arg Tyr Ile Trp Ile Ile Gly Met
            340                 345                 350

Leu Tyr Ala Tyr Tyr His Pro Thr Val Glu Ser Trp Met Asp Lys Leu
        355                 360                 365

Glu Glu Ala Glu Met Lys Phe Arg Val Ala Ile Lys Thr Ser Val Ala
    370                 375                 380

Leu Ile Ala Leu Thr Val Gly Tyr Phe Trp Tyr Glu Tyr Ile Tyr Lys
385                 390                 395                 400

Met Asp Lys Leu Thr Tyr Asn Lys Tyr His Pro Tyr Thr Ser Trp Ile
                405                 410                 415

Pro Ile Thr Val Tyr Ile Cys Leu Arg Asn Ile Thr Gln Ser Phe Arg
            420                 425                 430

Gly Tyr Ser Leu Thr Leu Leu Ala Trp Leu Gly Lys Ile Thr Leu Glu
        435                 440                 445

Thr Tyr Ile Ser Gln Phe His Ile Trp Leu Arg Ser Gly Val Pro Asp
    450                 455                 460

Gly Gln Pro Lys Leu Leu Leu Ser Leu Val Pro Asp Tyr Pro Leu Leu
465                 470                 475                 480

Asn Phe Met Leu Thr Thr Ser Ile Tyr Val Ala Ile Ser Tyr Arg Leu
                485                 490                 495
```

```
Phe Glu Leu Thr Asn Thr Leu Lys Thr Ala Phe Ile Pro Thr Lys Asp
            500                 505                 510

Asp Lys Arg Leu Val Tyr Asn Thr Ile Ser Ala Leu Ile Ile Cys Thr
        515                 520                 525

Cys Leu Tyr Phe Phe Ser Phe Ile Leu Ile Thr Ile Pro Gln Lys Leu
    530                 535                 540

Val Ser Gln Asn Phe Ile Phe Leu Cys Gly Arg Lys Leu Phe Phe Pro
545                 550                 555                 560

Trp Tyr Leu Ser Ser Leu Ile Cys
                565

<210> SEQ ID NO 6
<211> LENGTH: 1623
<212> TYPE: DNA
<213> ORGANISM: Arabidopsis thaliana
<220> FEATURE:
<223> OTHER INFORMATION: CAS1L1 (RWA1) coding sequence (NM_124004.2)

<400> SEQUENCE: 6
atggtggatc ctggaccaat tactccgggc caggtatctt ttcttcttgg agtaatccca      60
atatttgttg ttggatata ctcggagtta cttgagtaca gaaaatcttg ggttcccttg     120
aaacctcact cggataataa tctagttgaa ttgggagacg tagcagagaa ggacgacgac     180
aaagctgatc tgttggaggg aggtcttgcc cgatcaccat ctgtaaagtt tcataattca     240
tctatcagaa caaacataat caggtttttg agtatggaag attcattttt gctggaacat     300
cgagcaacct tgagagcaat gtcggaattt ggggcaatct taatatattt ctatatctgt     360
gaccgcacag aattgcttgg agattctacc aagaattaca accgcgacct tttccttttt     420
ctctacgttc ttctcatcat agtatcagcc atgacatctc tcagaaaaca caatgacaag     480
tcacccatat ctgggaagtc cattctttac cttaatcgcc accaaactga gaatggaaaa     540
ggatggatgc aggtttttgtt cttaatgtat cactactttg ctgcggccga gatatacaac     600
gcaatccgta tctttattgc tgcttatgtt tggatgactg gttttggaaa cttctcttac     660
tactatgtca gaaaggattt ctctgttgca cgttttgcgc agatgatgtg gaggctgaac     720
ttctttgtag cgttttgctg tattgttctc aacaacgact atatgttata ctacatctgc     780
ccaatgcaca ctcttttcac cctaatggta tatggagctc tgggtatctt cagcaagtac     840
aatgagatag gatcggtgat ggctctgaag atatttttcat gcttcctcgt tgtcttttg     900
ttgtgggaaa ttcctggagc ttttgaaata ttttggggtc ccttaacatt tttgctaggt     960
tacaatgacc ctgccaagcc cgatcttcat cggctgcatg aatggcactt tagatcaggc    1020
cttgatcgct acatatggat catcggaatg atttatgcct attatcaccc aactgtagag    1080
agatggatgg agaagttaga ggactgtgaa acgaagaaaa gactatccat aaaggccgct    1140
attgttacta ttactgtgct tgttggctat gtgtggtatg aatgtatcta caagctggac    1200
aggaccagtt acaacatgta tcatccgtac acatcatgga tccccatcac tgttttacata    1260
tgccttcgga atttcacccca ccagcttcga agtgtctcat tgactctctt tgcgtggctt    1320
ggcaagatca cttagagac ttacatttcc cagtttcata tatggctaag atcaaacatg    1380
cctgacgggc aaccaaaatg gcttctctct attattccgg atacccctat gctcaatttc    1440
atgctgacaa ctgctatata cgtccttgta tctcaccgtc tctttgaact aaccaacaca    1500
ctcaagacgg tttcgtacc cacaaaagac aacaagcgac tcttctctaa cttcatagct    1560
gggattgcca tcgctcttcc actctattgc ttctcattcg ttcttcttca gattcatcgt    1620
```

```
<210> SEQ ID NO 7
<211> LENGTH: 1635
<212> TYPE: DNA
<213> ORGANISM: Arabidopsis thaliana
<220> FEATURE:
<223> OTHER INFORMATION: CAS1L2 (RWA2) coding sequence (NM_001125120.1)

<400> SEQUENCE: 7
atggcgagtt caagccctgt tacacctggg ctaatgtcgg tggtgttcgg gattgtgccg      60
gtgatcgtgg cttggctata ctctgagtat ctgcactatg ctaaatactc ggtctccgcc     120
aaaacgcact ctgatgtcaa tttggtggaa attgcgaaag attttgttaa agaagatgac     180
aaagctcttt taatagaaga tggaggtggt ctccaatcag cttctcctag agccaaaggc     240
ccgaccacac attctcctct catcaggttt gtcctcttgg atgagtcgtt cttggttgag     300
aacaggctga ctttaagggc aataattgag tttgcagtac ttatggtata cttttacata     360
tgtgaccgca cagatgtctt caattcatca agaagagtt acaaccggga tctctttctg     420
ttcctttact ccttctcat catcgtttca gcgataactt cattcacgat acatactgat     480
aaatcaccat tcagcggaaa agccatcatg tacttgaata ggcatcaaac cgaggagtgg     540
aaaggctgga tgcaggtcct tttcttgatg taccactact tgctgctgc agagtactat     600
aatgcgatcc gtgttttcat tgcttgctat gtatggatga ctggatttgg aattttttct     660
tattattaca ttcgcaagga ctttagcctt gcaaggtttg cacagatgat gtggcggcta     720
aatttcctgg tcatattctc ctgcatcgtc ctcaacaaca gttacatgct atactacatc     780
tgcccaatgc acactctgtt tactctaatg gtctatgggg cacttggtat tatgagcaag     840
tataatgaga tgggttcagt catagctgcc aaattttttg cctgcttcgt tgttgttatc     900
atcgtttggg aaattcctgg cgttttgaa tggatttgga gtccatttac actcctaatg     960
ggttacaatg atccccgcaaa acctcagctt cccctcttgc atgagtggca tttccgctct    1020
ggacttgatc ggtacatatg gataatcggg atgctatatg catactacca cccaactgtt    1080
gaaagttgga tggataaact ggaggaagct gagatgaaat tcagggtggc tatcaaaaca    1140
tctgtggcac tgatagcact aacggtggga tattttggt acgagtatat atacaagatg    1200
gacaagttaa cttacaacaa atatcatcct tacacctctt ggattccaat aactgtttat    1260
atctgtctcc ggaacatcac ccagtctttc cgcggctaca gtttgacccct ctggcgtgg   1320
cttggaaaga taacactgga gacatatatc tcccagtttc atatatggct cagatctgga   1380
gttcctgatg gtcaacccaa attactacta tctcttgtcc cggattaccc attgttgaac   1440
ttcatgctca ctacttcgat ttacgtcgct atctcttata ggctctttga gcttaccaac   1500
actttgaaaa cagccttcat accaaccaag gacgacaaac gccttgtcta caacacgatc   1560
tcagcactca taatctgcac ttgtctctac tttttctcat ttattcttat cacaattccc   1620
caaaaactgg tgtga                                                   1635

<210> SEQ ID NO 8
<211> LENGTH: 1707
<212> TYPE: DNA
<213> ORGANISM: Arabidopsis thaliana
<220> FEATURE:
<223> OTHER INFORMATION: CAS1L2 (RWA2) coding sequence (NM_001084647.4)

<400> SEQUENCE: 8
atggcgagtt caagccctgt tacacctggg ctaatgtcgg tggtgttcgg gattgtgccg      60
```

```
gtgatcgtgg cttggctata ctctgagtat ctgcactatg ctaaatactc ggtctccgcc    120
aaaactaggc actctgatgt caatttggtg gaaattgcga aagattttgt taaagaagat    180
gacaaagctc ttttaataga agatggaggt ggtctccaat cagcttctcc tagagccaaa    240
ggcccgacca cacattctcc tctcatcagg tttgtcctct tggatgagtc gttcttggtt    300
gagaacaggc tgactttaag ggcaataatt gagtttgcag tacttatggt atacttttac    360
atatgtgacc gcacagatgt cttcaattca tcaaagaaga gttacaaccg ggatctcttt    420
ctgttccttt acttccttct catcatcgtt tcagcgataa cttcattcac gatacatact    480
gataaatcac cattcagcgg aaaagccatc atgtacttga ataggcatca aaccgaggag    540
tggaaaggct ggatgcaggt ccttttcttg atgtaccact actttgctgc tgcagagtac    600
tataatgcga tccgtgtttt cattgcttgc tatgtatgga tgactggatt tgggaatttt    660
tcttattatt acattcgcaa ggactttagc cttgcaaggt ttgcacagat gatgtggcgg    720
ctaaatttcc tggtcatatt ctcctgcatc gtcctcaaca acagttacat gctatactac    780
atctgcccaa tgcacactct gtttactcta atggtctatg gggcacttgg tattatgagc    840
aagtataatg agatgggttc agtcatagct gccaaatttt ttgcctgctt cgttgttgtt    900
atcatcgttt gggaaattcc tggcgttttt gaatggattt ggagtccatt tacactccta    960
atgggttaca atgatcccgc aaaacctcag cttcccctct tgcatgagtg gcatttccgc   1020
tctggacttg atcggtacat atggataatc gggatgctat atgcatacta ccacccaact   1080
gttgaaagtt ggatggataa actggaggaa gctgagatga aattcagggt ggctatcaaa   1140
acatctgtgg cactgatagc actaacggtg ggatatttt ggtacgagta tatatacaag   1200
atggacaagt taacttacaa caaatatcat ccttacacct cttggattcc aataactgtt   1260
tatatctgtc tccggaacat cacccagtct ttccgcggct acagtttgac ccttctggcg   1320
tggcttggaa agataacact ggagacatat atctcccagt ttcatatatg gctcagatct   1380
ggagttcctg atggtcaacc caaattacta ctatctcttg tcccggatta cccattgttg   1440
aacttcatgc tcactacttc gatttacgtc gctatctctt ataggctctt tgagcttacc   1500
aacactttga aaacagcctt cataccaacc aaggacgaca aacgccttgt ctacaacacg   1560
atctcagcac tcataatctg cacttgtctc tacttttttct catttattct tatcacaatt   1620
ccccaaaaac tggtaagtca aaattttatc tttttgtgtg ggagaaagct ttttttttccc   1680 tggtacttga gttcattgat atgttag                                       1707
```

<210> SEQ ID NO 9
<211> LENGTH: 1623
<212> TYPE: DNA
<213> ORGANISM: Arabidopsis thaliana
<220> FEATURE:
<223> OTHER INFORMATION: CAS1L3 (RWA3) nucleic acid coding sequence

<400> SEQUENCE: 9

```
atggcggatt ctcagccaat cacgcctggt caggtttcgt ttctactcgg agtcattcct     60
gtcttcatag catggattta ctcagagttt ctagagtata agaggtcttc attgcactct    120
aaagttcatt cagataataa tttggttgaa cttggtgagg taaaaaacaa ggaagatgaa    180
ggagtagttt tacttgaagg aggtcttcca agatcagtct ctacaaagtt ttataactca    240
cctatcaaaa caaacttgat tagatttctg acgctggaag actctttctt gattgaaaat    300
cgagcaacct tgagagcgat ggctgagttt ggggctattc ttttttactt ttatattagt    360
```

| | | |
|---|---|---|
| gatcgaacaa gcttgcttgg agagtctaaa aagaattaca acagagatct tttcctctctt | 420 | |
| ctctactgtc ttctcatcat agtttcagcc atgacatcct tgaagaaaca caatgacaaa | 480 | |
| tcacctataa caggaaaatc cattctctat cttaatcgtc accagactga agagtggaag | 540 | |
| ggatggatgc aggttctatt tcttatgtat cattactttg ctgcggctga gatatataat | 600 | |
| gcaatcaggg ttttcattgc tgcctacgtc tggatgactg ggtttgggaa cttctcttat | 660 | |
| tactatatca gaaaggattt ctccctagca cgatttactc agatgatgtg gcgtcttaac | 720 | |
| ttatttgtgg cgtttagctg cattattctc aataatgatt atatgctgta ctacatctgt | 780 | |
| ccaatgcaca ctctgttcac tcttatggtg tatggagccc ttggtatctt cagtcgatat | 840 | |
| aacgaaatac catcagtaat ggctttgaag attgcttcat gctttctcgt ggttatcgtg | 900 | |
| atgtgggaga ttcctggcgt ttttgagatt ttctggagtc cttttaacatt cttactggga | 960 | |
| tacactgatc cagctaaacc agaactacca cttttacatg aatggcactt cagatcagga | 1020 | |
| cttgaccgct acatatggat cattggaatg atatatgcct atttccatcc cactgtagag | 1080 | |
| agatggatgg agaaattgga ggagtgtgat gccaagagaa gatgtcaat aaagacaagc | 1140 | |
| ataattgcaa tttcctcatt tgttggttac ctatggtatg aatacatata caagcttgac | 1200 | |
| aaggttacat acaacaaata tcatccctac acatcgtgga ttccaataac cgtctacatc | 1260 | |
| tgtctgcgaa attctacaca acagctgcgt aatttctcca tgacactatt tgcgtggctc | 1320 | |
| ggcaagatta ctctggaaac ctatatttct cagtttcaca tctggttaag atcgaatgtg | 1380 | |
| ccaaatggac agcctaagtg gctattatgc attattccag aatacccaat gctcaacttc | 1440 | |
| atgctcgtca cggccatcta tgtcttggtg tcccaccgac ttttcgagct acaaacacg | 1500 | |
| ttaaagtctg ttttcatacc aacaaaagac gacaagaggc tgctccacaa tgttctcgct | 1560 | |
| ggagctgcca tctcgttctg tttatattta acatctctca ttcttctcca gatcccacac | 1620 | |
| taa | 1623 | |

<210> SEQ ID NO 10
<211> LENGTH: 1413
<212> TYPE: DNA
<213> ORGANISM: Arabidopsis thaliana
<220> FEATURE:
<223> OTHER INFORMATION: CAS1L4 (RWA4) coding sequence (NM_102729.2)

<400> SEQUENCE: 10

| | | |
|---|---|---|
| atgttctcta gccataatat tttcttaacc attggcattg tgtttattcg taggtttctg | 60 | |
| actttggaag actctttctt gcttgaaaac cgagcaacct tgagagcaat ggctgagttt | 120 | |
| ggagcaattc ttttatattt ttatatttgt gatcgaacta gcttgatcgg gcagtctcaa | 180 | |
| aagaattaca gccgagacct ttttctcttt ctcttctgtc ttctcatcat agtgtcagct | 240 | |
| atgacgtcct tgaagaaaca cactgacaag tcaccaataa caggaaagtc cattctgtat | 300 | |
| ctcaatcgtc accagactga agaatggaaa gggtggatgc aggttctatt tctgatgtat | 360 | |
| cattattttg cggcagttga gttttacaat gcaatcaggg tcttcatcgc tggctatgtg | 420 | |
| tggatgaccg gttttgggaa cttctcttat tactatatcc gaaaggattt ctcccttgca | 480 | |
| cgattcactc agatgatgtg gcggcttaac tttttgtgg cgttttgttg cattattctc | 540 | |
| aacaatgact atatgctgta ctacatctgt ccaatgcaca ctctattcac gctgatggtc | 600 | |
| tatggagccc ttggtatttta cagtcagtat aacgaaatag catcagtgat ggctctgaag | 660 | |
| attgcttcat gctttctcgt ggttatcctt atgtgggaga ttcctggagt ttttgagatt | 720 | |
| ttctggagtc ctctggcatt cttactgggg tacacagatc cagctaaacc agaccttcca | 780 | |

```
cgtctacacg aatggcattt cagatctgga cttgatcgct acatatggat catcggcatg    840
atatatgcat attttcatcc cactgtagaa agatggatgg agaaattgga ggagtgtgat    900
gctaagagaa ggatgtcaat caagacaagc ataataggaa tttcttcatt cgctggttac    960
ctttggtatg aatacatcta caagctggac aaggttacgt acaacaaata tcatccctac   1020
acatcttgga ttccaataac tgtctacatc tgtctgcgaa attgcaccca acagctacgg   1080
agattttccc tgacactctt tgcgtggctg ggcaagataa ctctcgagac ctacatttca   1140
cagtttcaca tctggttaag atcgagtgtg ccaaatgggc agccaaagtt gctattatca   1200
atcatcccag aatacccaat gctcaacttc atgctcacca cggccatcta cgtcttggta   1260
tctgttcgac ttttcgagct aaccaataca ttaaaatcag ttttcatacc cacgaaagac   1320
gacaaacggc tgctccacaa cgtgattgct atggctgcga tatcattttg tttatatatt   1380
atcggtctta ttcttctctt gatcccacat taa                                1413
```

<210> SEQ ID NO 11
<211> LENGTH: 102
<212> TYPE: PRT
<213> ORGANISM: Artificial Sequence
<220> FEATURE:
<223> OTHER INFORMATION: synthetic sequence of highly conserved region
      of CAS1L protein sequence

<400> SEQUENCE: 11

Tyr Leu Asn Arg His Gln Thr Glu Glu Trp Lys Gly Trp Met Gln Val
1               5                   10                  15

Leu Phe Leu Met Tyr His Tyr Phe Ala Ala Glu Tyr Tyr Asn Ala
            20                  25                  30

Ile Arg Val Phe Ile Ala Cys Tyr Val Trp Met Thr Gly Phe Gly Asn
        35                  40                  45

Phe Ser Tyr Tyr Tyr Ile Arg Lys Asp Phe Ser Leu Ala Arg Phe Ala
    50                  55                  60

Gln Met Met Trp Arg Leu Asn Phe Leu Val Ile Phe Ser Cys Ile Val
65                  70                  75                  80

Leu Asn Asn Ser Tyr Met Leu Tyr Tyr Ile Cys Pro Met His Thr Leu
                85                  90                  95

Phe Thr Leu Met Val Tyr
            100

<210> SEQ ID NO 12
<211> LENGTH: 102
<212> TYPE: PRT
<213> ORGANISM: Artificial Sequence
<220> FEATURE:
<223> OTHER INFORMATION: synthetic consensus sequence of conserved
      region from CAS1L protein sequence
<220> FEATURE:
<221> NAME/KEY: VARIANT
<222> LOCATION: 17, 25, 27, 29, 35, 39, 54, 55, 60, 61, 64, 72, 73, 75,
      76, 77, 79, 80, 82, 84, 86, 99
<223> OTHER INFORMATION: Xaa = Any Amino Acid
<220> FEATURE:
<221> NAME/KEY: VARIANT
<222> LOCATION: 17, 25, 27, 29, 35, 39, 54, 55, 60, 61, 64, 72, 73, 75,
      76, 77, 79, 80, 82, 84, 86, 99
<223> OTHER INFORMATION: Xaa = Any Amino Acid

<400> SEQUENCE: 12

Tyr Leu Asn Arg His Gln Thr Glu Glu Trp Lys Gly Trp Met Gln Val
1               5                   10                  15

```
Xaa Phe Leu Met Tyr His Tyr Phe Xaa Ala Xaa Glu Xaa Tyr Asn Ala
            20                  25                  30

Ile Arg Xaa Phe Ile Ala Xaa Tyr Val Trp Met Thr Gly Phe Gly Asn
        35                  40                  45

Phe Ser Tyr Tyr Tyr Xaa Xaa Lys Asp Phe Ser Xaa Xaa Arg Phe Xaa
    50                  55                  60

Gln Met Met Trp Arg Leu Asn Xaa Xaa Val Xaa Xaa Xaa Cys Xaa Xaa
65                  70                  75                  80

Leu Xaa Asn Xaa Tyr Xaa Leu Tyr Tyr Ile Cys Pro Met His Thr Leu
                85                  90                  95

Phe Thr Xaa Met Val Tyr
            100

<210> SEQ ID NO 13
<211> LENGTH: 16
<212> TYPE: PRT
<213> ORGANISM: Artificial Sequence
<220> FEATURE:
<223> OTHER INFORMATION: synthetic sequence of conserved motif from
      CAS1L protein sequence

<400> SEQUENCE: 13

Leu His Glu Trp His Phe Arg Ser Gly Leu Asp Arg Tyr Ile Trp Ile
1               5                   10                  15

<210> SEQ ID NO 14
<211> LENGTH: 235
<212> TYPE: PRT
<213> ORGANISM: Artificial Sequence
<220> FEATURE:
<223> OTHER INFORMATION: synthetic sequence of a central region from
      CAS1L protein sequence

<400> SEQUENCE: 14

Tyr Phe Tyr Ile Ser Asp Arg Thr Ser Leu Leu Gly Glu Ser Lys Lys
1               5                   10                  15

Asn Tyr Asn Arg Asp Leu Phe Leu Phe Leu Tyr Cys Leu Leu Ile Ile
                20                  25                  30

Val Ser Ala Met Thr Ser Leu Lys Lys His Asn Asp Lys Ser Pro Ile
            35                  40                  45

Thr Gly Lys Ser Ile Leu Tyr Leu Asn Arg His Gln Thr Glu Glu Trp
        50                  55                  60

Lys Gly Trp Met Gln Val Leu Phe Leu Met Tyr His Tyr Phe Ala Ala
65                  70                  75                  80

Ala Glu Ile Tyr Asn Ala Ile Arg Val Phe Ile Ala Tyr Val Trp
                85                  90                  95

Met Thr Gly Phe Gly Asn Phe Ser Tyr Tyr Tyr Ile Arg Lys Asp Phe
            100                 105                 110

Ser Leu Ala Arg Phe Thr Gln Met Met Trp Arg Leu Asn Leu Phe Val
        115                 120                 125

Ala Phe Ser Cys Ile Ile Leu Asn Asn Asp Tyr Met Leu Tyr Tyr Ile
130                 135                 140

Cys Pro Met His Thr Leu Phe Thr Leu Met Val Tyr Gly Ala Leu Gly
145                 150                 155                 160

Ile Phe Ser Arg Tyr Asn Glu Ile Pro Ser Val Met Ala Leu Lys Ile
                165                 170                 175

Ala Ser Cys Phe Leu Val Val Ile Val Met Trp Glu Ile Pro Gly Val
            180                 185                 190
```

```
Phe Glu Ile Phe Trp Ser Pro Leu Thr Phe Leu Leu Gly Tyr Thr Asp
            195                 200                 205

Pro Ala Lys Pro Glu Leu Pro Leu Leu His Glu Trp His Phe Arg Ser
    210                 215                 220

Gly Leu Asp Arg Tyr Ile Trp Ile Ile Gly Met
225                 230                 235

<210> SEQ ID NO 15
<211> LENGTH: 539
<212> TYPE: PRT
<213> ORGANISM: Artificial Sequence
<220> FEATURE:
<223> OTHER INFORMATION: partial Os01g0631100_Oryza sequence from CAS1L
      gene family

<400> SEQUENCE: 15

Met Glu Val Phe Gly Pro Val Thr Ala Gly Gln Val Ser Phe Leu Leu
1               5                   10                  15

Gly Leu Phe Pro Val Leu Ile Ala Trp Ile Tyr Ser Glu Val Leu Glu
            20                  25                  30

Tyr Arg Lys Ser Ser Ser Met Lys Val His Ser Asp Ser Asn Leu Glu
        35                  40                  45

Asn Gly Thr Val Lys Glu Asp Asp Lys Thr Val Leu Leu Glu Gly Gly
    50                  55                  60

Leu Ser Lys Ser Pro Ser Thr Lys Phe Arg Ile Asn Ser Thr Lys Ala
65                  70                  75                  80

Asn Leu Ile Arg Phe Ile Thr Met Asp Glu Ser Phe Leu Leu Glu Asn
                85                  90                  95

Arg Ala Val Leu Arg Ala Met Ala Glu Phe Gly Ile Val Leu Val Tyr
            100                 105                 110

Phe Tyr Ile Cys Asp Arg Thr Asn Ile Phe Pro Glu Ser Lys Lys Ser
            115                 120                 125

Tyr Asn Arg Asp Leu Phe Leu Phe Leu Tyr Ile Leu Leu Ile Ile Ala
        130                 135                 140

Ser Ala Leu Thr Ser Leu Lys Lys His His Asp Lys Ser Ala Phe Ser
145                 150                 155                 160

Gly Lys Ser Ile Leu Tyr Leu Asn Arg His Gln Thr Glu Glu Trp Lys
                165                 170                 175

Gly Trp Met Gln Val Leu Phe Leu Met Tyr His Tyr Phe Ala Ala Thr
            180                 185                 190

Glu Ile Tyr Asn Ala Ile Arg Val Phe Ile Ala Ala Tyr Val Trp Met
        195                 200                 205

Thr Gly Phe Gly Asn Phe Ser Tyr Tyr Tyr Ile Lys Lys Asp Phe Ser
    210                 215                 220

Leu Ala Arg Phe Ala Gln Met Met Trp Arg Leu Asn Phe Phe Val Ala
225                 230                 235                 240

Phe Cys Cys Ile Val Leu Asp Asn Asp Tyr Met Leu Tyr Tyr Ile Cys
                245                 250                 255

Pro Met His Thr Leu Phe Thr Leu Met Val Tyr Gly Ser Leu Gly Leu
            260                 265                 270

Phe Asn Lys Tyr Asn Glu Ile Pro Ser Val Met Ala Met Lys Ile Val
        275                 280                 285

Ser Cys Phe Leu Ala Val Ile Leu Ile Trp Glu Ile Pro Gly Val Phe
    290                 295                 300

Glu Leu Leu Trp Ser Pro Phe Phe Leu Leu Gly Tyr Lys Asp Pro
305                 310                 315                 320
```

Glu Pro Ser Lys Ala Asn Leu Pro Leu Leu His Glu Trp His Phe Arg
                325                 330                 335

Ser Gly Leu Asp Arg Tyr Ile Trp Ile Ile Gly Met Ile Tyr Ala Tyr
            340                 345                 350

Phe His Pro Asn Val Glu Arg Trp Met Glu Lys Leu Glu Glu Ser Glu
        355                 360                 365

Thr Lys Val Arg Leu Ser Ile Lys Gly Thr Ile Ile Ser Ile Ser Leu
    370                 375                 380

Val Ala Gly Tyr Leu Trp Tyr Glu Tyr Ile Tyr Lys Leu Asp Lys Ile
385                 390                 395                 400

Thr Tyr Asn Lys Tyr His Pro Tyr Thr Ser Trp Ile Pro Ile Thr Val
            405                 410                 415

Tyr Ile Ser Leu Arg Asn Cys Thr Gln Gln Leu Arg Asn Val Ser Leu
        420                 425                 430

Thr Leu Phe Ala Trp Leu Gly Lys Ile Thr Leu Glu Thr Tyr Ile Ser
    435                 440                 445

Gln Ile His Ile Trp Leu Arg Ser Asn Met Pro Asn Gly Gln Pro Lys
450                 455                 460

Trp Leu Leu Ser Phe Ile Pro Gly Tyr Pro Leu Leu Asn Phe Met Leu
465                 470                 475                 480

Ala Thr Ala Ile Tyr Leu Leu Ile Ser Tyr Arg Val Phe Glu Leu Thr
            485                 490                 495

Gly Val Leu Lys Ser Ala Phe Ile Pro Ser Arg Asp Asn Asn Arg Leu
        500                 505                 510

Tyr Gln Asn Phe Val Ala Gly Ile Ala Ile Ser Val Cys Leu Tyr Phe
    515                 520                 525

Leu Ser Ile Val Leu Leu Lys Ile Pro Ile Val
530                 535

<210> SEQ ID NO 16
<211> LENGTH: 539
<212> TYPE: PRT
<213> ORGANISM: Artificial Sequence
<220> FEATURE:
<223> OTHER INFORMATION: partial Os05g0582100_Oryza sequence from CAS1L
      gene family

<400> SEQUENCE: 16

Met Glu Val Phe Gly Pro Val Thr Pro Gly Gln Val Ser Phe Leu Leu
1               5                   10                  15

Gly Leu Phe Pro Val Leu Ile Gly Trp Ile Tyr Ala Glu Ile Leu Glu
            20                  25                  30

Tyr Arg Lys Ser Leu Leu Tyr Gly Lys Val His Ser Asp Ala Asn Leu
        35                  40                  45

Glu Asn Glu Thr Met Lys Glu Asp Lys Ala Val Leu Leu Gly Gly
    50                  55                  60

Gln Ser Lys Ser Pro Ser Thr Lys Leu Arg Asn Met Ser Thr Lys Ala
65                  70                  75                  80

Asn Leu Ile Arg Phe Ile Thr Met Asp Glu Ser Phe Leu Leu Glu Asn
                85                  90                  95

Arg Ala Val Leu Arg Ala Met Ala Glu Val Gly Ile Ile Leu Val Tyr
            100                 105                 110

Phe Tyr Ile Cys Asp Arg Thr Asn Ile Phe Pro Glu Thr Lys Lys Ser
        115                 120                 125

Tyr Asn Arg Asp Leu Phe Leu Phe Leu Tyr Ile Leu Leu Ile Ile Ala

```
            130                 135                 140
Ser Ala Leu Thr Ser Leu Lys Lys His Asn Glu Lys Ser Ala Phe Thr
145                 150                 155                 160

Gly Lys Ser Ile Leu Tyr Leu Asn Arg His Gln Thr Glu Glu Trp Lys
                165                 170                 175

Gly Trp Met Gln Val Leu Phe Leu Met Tyr His Tyr Phe Ala Ala Thr
            180                 185                 190

Glu Ile Tyr Asn Ala Ile Arg Val Phe Ile Ala Ala Tyr Val Trp Met
        195                 200                 205

Thr Gly Phe Gly Asn Phe Ser Tyr Tyr Tyr Ile Lys Lys Asp Phe Ser
    210                 215                 220

Ile Ala Arg Phe Ala Gln Met Met Trp Arg Leu Asn Phe Phe Val Ala
225                 230                 235                 240

Phe Cys Cys Ile Val Leu Asp Asn Asp Tyr Met Leu Tyr Tyr Ile Cys
                245                 250                 255

Pro Met His Thr Leu Phe Thr Leu Met Val Tyr Gly Ser Leu Gly Leu
            260                 265                 270

Phe Asn Lys Tyr Asn Glu Lys Pro Ser Val Met Ala Ile Lys Ile Ala
        275                 280                 285

Cys Cys Phe Leu Thr Val Ile Leu Ile Trp Glu Ile Pro Gly Val Phe
    290                 295                 300

Glu Phe Leu Trp Ala Pro Phe Thr Phe Leu Leu Gly Tyr Lys Asp Pro
305                 310                 315                 320

Glu Pro Ser Lys Ala Asn Leu Pro Leu Leu His Glu Trp His Phe Arg
                325                 330                 335

Ser Gly Leu Asp Arg Tyr Ile Trp Ile Ile Gly Met Ile Tyr Ala Tyr
            340                 345                 350

Phe His Pro Asn Val Glu Arg Trp Met Glu Lys Leu Glu Glu Ser Glu
        355                 360                 365

Thr Lys Val Arg Leu Phe Ile Lys Gly Ala Ile Val Thr Leu Ser Leu
    370                 375                 380

Thr Ala Gly Tyr Leu Trp Tyr Glu Tyr Ile Tyr Arg Leu Asp Lys Ile
385                 390                 395                 400

Thr Tyr Asn Lys Tyr His Pro Tyr Thr Ser Trp Ile Pro Ile Thr Val
                405                 410                 415

Tyr Ile Cys Leu Arg Asn Cys Thr Gln Gln Leu Arg Ser Ala Ser Leu
            420                 425                 430

Ala Leu Phe Ala Trp Leu Gly Lys Ile Thr Leu Glu Thr Tyr Ile Ser
        435                 440                 445

Gln Ile His Ile Trp Leu Arg Ser Ser Thr Pro Asn Gly Gln Pro Lys
    450                 455                 460

Trp Leu Leu Ser Phe Val Pro Asp Tyr Pro Leu Leu Asn Phe Met Leu
465                 470                 475                 480

Thr Thr Ala Ile Tyr Leu Leu Leu Ser Tyr Arg Val Phe Glu Ile Thr
                485                 490                 495

Gly Val Leu Lys Gly Ala Phe Ile Pro Ser Arg Asp Asn Asn Arg Leu
            500                 505                 510

Tyr Gln Asn Phe Ile Ala Gly Ile Ala Ile Ser Ala Cys Leu Tyr Phe
        515                 520                 525

Cys Ser Leu Ile Leu Val Lys Ile Thr Ile Val
    530                 535

<210> SEQ ID NO 17
```

```
<211> LENGTH: 552
<212> TYPE: PRT
<213> ORGANISM: Artificial Sequence
<220> FEATURE:
<223> OTHER INFORMATION: partial Os03g0314200_Oryza sequence from CAS1L
      gene family

<400> SEQUENCE: 17
```

Met Ala Glu Ala Ile Ala Ser Ala Gly Gly Ile Ala Met Ala Ala Ser
1               5                   10                  15

Thr Ser Leu Thr Pro Gly Gln Val Ser Ala Leu Leu Gly Phe Leu Trp
            20                  25                  30

Val Phe Thr Ala Trp Ala Tyr Ala Glu Val Leu Tyr Tyr Arg Lys Asn
        35                  40                  45

Ala Ala Ser Ile Lys Ala His Ser Asp Val Asn Leu Ala Val Met Asp
    50                  55                  60

Ser Ser Ser Asn Lys Gly Glu Asp Gln Val Met Leu Leu Glu Glu Gly
65                  70                  75                  80

Val Gln Ala Pro Val Gln Lys Pro Val Tyr Ala Ser Leu Thr Ser Gln
                85                  90                  95

Met Phe Arg Leu Phe Leu Asp Gln Ala Leu Ile Leu Glu Asn Arg
            100                 105                 110

Leu Thr Leu Arg Ala Ile Ser Glu Phe Gly Gly His Leu Leu Tyr Phe
        115                 120                 125

Tyr Ile Cys Asp Arg Thr Asn Leu Leu Gly Glu Ser Ala Lys Asn Tyr
    130                 135                 140

Ser Arg Asp Met Phe Leu Phe Leu Tyr Phe Leu Leu Ile Ile Val Ala
145                 150                 155                 160

Ala Met Thr Ser Phe Lys Val His Gln Asp Lys Ser Ser Phe Thr Gly
                165                 170                 175

Lys Ser Ile Leu Tyr Leu Asn Arg His Gln Thr Glu Glu Trp Lys Gly
            180                 185                 190

Trp Met Gln Val Leu Phe Leu Met Tyr His Tyr Phe Asn Ala Lys Glu
        195                 200                 205

Ile Tyr Asn Ala Ile Arg Val Phe Ile Ala Ala Tyr Val Trp Met Thr
    210                 215                 220

Gly Phe Gly Asn Phe Ser Tyr Tyr Val Arg Lys Asp Phe Ser Leu
225                 230                 235                 240

Ala Arg Phe Ala Gln Met Met Trp Arg Leu Asn Phe Phe Val Ala Phe
                245                 250                 255

Cys Cys Ile Val Leu Asn Asn Asp Tyr Thr Leu Tyr Tyr Ile Cys Pro
            260                 265                 270

Met His Thr Leu Phe Thr Leu Met Val Tyr Gly Ala Leu Gly Ile Leu
        275                 280                 285

Asn Lys Tyr Asn Glu Ile Gly Ser Val Met Ala Ile Lys Phe Val Ala
    290                 295                 300

Cys Phe Leu Val Val Ile Leu Ile Trp Glu Ile Pro Gly Val Phe Glu
305                 310                 315                 320

Ile Val Trp Ser Pro Phe Thr Phe Leu Leu Gly Tyr Thr Asp Pro Ser
                325                 330                 335

Lys Pro Asp Leu Pro Arg Leu His Glu Trp His Phe Arg Ser Gly Leu
            340                 345                 350

Asp Arg Tyr Ile Trp Ile Val Gly Met Ile Tyr Ala Tyr Tyr His Pro
        355                 360                 365

Thr Val Glu Lys Trp Met Glu Lys Leu Glu Glu Ala Glu Thr Lys Thr

```
                 370               375               380
Lys Leu Tyr Ile Lys Ala Leu Ile Val Ser Ile Ala Leu Thr Ala Gly
385                 390               395               400

Cys Leu Trp Tyr Glu Tyr Ile Tyr Lys Leu Asp Lys Ile Thr Tyr Asn
              405               410               415

Lys Tyr His Pro Tyr Thr Ser Trp Ile Pro Ile Thr Val Tyr Ile Cys
              420               425               430

Leu Arg Asn Phe Thr Gln Glu Phe Arg Cys Cys Ser Leu Thr Leu Phe
              435               440               445

Ala Trp Leu Gly Lys Ile Thr Leu Glu Thr Tyr Ile Ser Gln Phe His
              450               455               460

Ile Trp Leu Arg Ser Lys Val Pro Asn Gly Gln Pro Lys Trp Leu Leu
465               470               475               480

Thr Ile Ile Pro Asn Tyr Pro Met Leu Asn Phe Met Leu Thr Thr Ala
              485               490               495

Ile Tyr Val Ala Val Ser His Arg Leu Phe Glu Leu Thr Asn Thr Leu
              500               505               510

Lys Ile Ala Phe Val Pro Ser Arg Asp Asn Lys Arg Leu Ser Tyr Asn
              515               520               525

Phe Val Ala Gly Ile Ala Ile Ser Val Ala Leu Tyr Ser Leu Ser Phe
530               535               540

Leu Ile Val Gly Val Ala Gly Tyr
545               550

<210> SEQ ID NO 18
<211> LENGTH: 473
<212> TYPE: PRT
<213> ORGANISM: Artificial Sequence
<220> FEATURE:
<223> OTHER INFORMATION: partial P2_P._trichocarpa sequence from CAS1L
      gene family

<400> SEQUENCE: 18

Arg Ser Ala Ser Ala Lys Phe His Ser Ser Ala Ile Lys Met Asn Leu
1               5                   10                  15

Ile Arg Phe Met Thr Leu Asp Asp Ser Phe Leu Leu Glu Asn Arg Ala
              20                  25                  30

Thr Leu Arg Ala Met Ser Glu Phe Gly Ala Val Leu Leu Tyr Phe Tyr
              35                  40                  45

Ile Cys Asp Arg Thr Asn Ile Leu Gly Glu Ser Thr Lys Ser Tyr Asn
50                  55                  60

Arg Asp Leu Phe Val Phe Leu Tyr Ile Leu Leu Ile Ile Val Ser Ser
65                  70                  75                  80

Met Thr Ser Leu Arg Lys His Thr Asp Lys Ser Ala Phe Thr Gly Lys
              85                  90                  95

Ser Met Leu Tyr Leu Asn Arg His Gln Thr Glu Glu Trp Lys Gly Trp
              100                 105                 110

Met Gln Val Leu Phe Leu Met Tyr His Tyr Phe Ala Ala Ala Glu Ile
              115                 120                 125

Tyr Asn Ala Ile Arg Ile Phe Ile Ala Ala Tyr Val Trp Met Thr Gly
              130                 135                 140

Phe Gly Asn Phe Ser Tyr Tyr Tyr Ile Arg Lys Asp Phe Ser Val Ala
145                 150                 155                 160

Arg Phe Ser Gln Met Met Trp Arg Leu Asn Phe Phe Val Ala Phe Cys
              165                 170                 175
```

Cys Ile Ile Leu Asn Asn Asp Tyr Met Leu Tyr Tyr Ile Cys Pro Met
                180                 185                 190

His Thr Leu Phe Thr Leu Met Val Tyr Gly Ala Leu Gly Ile Phe Asn
            195                 200                 205

Lys Tyr Asn Glu Asn Ser Ser Val Met Ala Val Lys Ile Leu Ser Cys
        210                 215                 220

Phe Leu Val Val Ile Leu Ile Trp Glu Ile Pro Gly Val Phe Asp Phe
225                 230                 235                 240

Leu Trp Ser Pro Leu Thr Phe Leu Leu Gly Tyr Ser Asp Pro Ala Lys
                245                 250                 255

Pro Asp Leu Pro Arg Leu His Glu Trp His Phe Arg Ser Gly Leu Asp
            260                 265                 270

Arg Tyr Ile Trp Ile Ile Gly Met Ile Tyr Ala Tyr Phe His Pro Asn
        275                 280                 285

Ile Glu Lys Trp Met Glu Lys Leu Glu Glu Ser Glu Thr Lys Lys Lys
            290                 295                 300

Leu Ser Met Lys Thr Gly Ile Val Ala Val Ser Val Ser Val Gly Tyr
305                 310                 315                 320

Leu Trp Tyr Glu Tyr Ile Tyr Lys Leu Asp Lys Val Ser Tyr Asn Lys
                325                 330                 335

Tyr His Pro Tyr Thr Ser Trp Ile Pro Ile Thr Val Tyr Ile Cys Leu
            340                 345                 350

Arg Asn Cys Thr Gln Gln Leu Arg Ser Phe Ser Ser Thr Leu Phe Ala
        355                 360                 365

Trp Leu Gly Lys Ile Thr Leu Glu Thr Tyr Ile Ser Gln Phe His Ile
            370                 375                 380

Trp Leu Arg Ser Asp Ile Pro Asn Gly Gln Pro Lys Trp Leu Leu Ser
385                 390                 395                 400

Phe Ile Pro Glu Tyr Pro Leu Leu Asn Phe Met Leu Thr Thr Ala Ile
                405                 410                 415

Tyr Val Leu Val Ser His Arg Leu Phe Glu Leu Thr Asn Thr Leu Lys
            420                 425                 430

Thr Val Phe Ile Pro Thr Lys Asp Asn Lys Arg Leu Phe Tyr Asn Ser
        435                 440                 445

Val Ala Gly Ala Ala Ile Ser Val Cys Leu Tyr Cys Val Ala Val Ile
    450                 455                 460

Leu Leu His Ile Pro His Ser Pro Ala
465                 470

```
<210> SEQ ID NO 19
<211> LENGTH: 482
<212> TYPE: PRT
<213> ORGANISM: Artificial Sequence
<220> FEATURE:
<223> OTHER INFORMATION: partial P3_P._trichocarpa sequence from CAS1L
      gene family

<400> SEQUENCE: 19
```

Leu Pro Arg Ser Ala Ser Ala Lys Phe His Ser Ser Ala Thr Lys Met
1               5                   10                  15

Asn Leu Ile Arg Phe Met Thr Met Asp Asp Ser Phe Leu Leu Glu Asn
            20                  25                  30

Arg Thr Thr Leu Arg Val Met Ser Glu Phe Gly Ala Val Leu Val Tyr
        35                  40                  45

Phe Tyr Ile Cys Asp Arg Thr Ile Arg Phe Met Thr Met Asp Asp Ser
    50                  55                  60

Phe Leu Leu Glu Asn Arg Thr Thr Leu Arg Val Met Ser Glu Phe Gly
65                  70                  75                  80

Ala Val Leu Val Tyr Phe Tyr Ile Cys Asp Arg Thr His Gln Thr Glu
            85                  90                  95

Glu Trp Lys Gly Trp Met Gln Val Ile Phe Leu Met Tyr His Tyr Phe
            100                 105                 110

Ala Ala Thr Glu Ile Tyr Asn Ala Ile Arg Val Phe Ile Ala Ala Tyr
            115                 120                 125

Val Trp Met Thr Gly Phe Gly Asn Phe Ser Tyr Tyr Ile Arg Lys
            130                 135                 140

Asp Phe Ser Val Ala Arg Phe Ala Gln Met Met Trp Arg Leu Asn Leu
145                 150                 155                 160

Phe Val Ala Phe Cys Cys Ile Val Leu Asn Asn Asp Tyr Met Leu Tyr
                165                 170                 175

Tyr Ile Cys Pro Met His Thr Leu Phe Thr Val Met Val Tyr Gly Val
                180                 185                 190

Leu Gly Ile Phe Asn Lys Tyr Asn Glu Asn Ser Ser Val Ile Ala Val
            195                 200                 205

Lys Ile Leu Ser Cys Phe Leu Met Val Ile Leu Ile Trp Glu Thr Pro
210                 215                 220

Gly Val Phe Asp Ile Leu Trp Ser Pro Leu Thr Phe Leu Leu Gly Tyr
225                 230                 235                 240

Thr Asp Pro Ala Lys Pro Asp Leu Pro Arg Leu His Glu Trp His Phe
                245                 250                 255

Arg Ser Gly Leu Asp Arg Tyr Ile Trp Ile Gly Met Ile Tyr Ala
                260                 265                 270

Tyr Phe His Pro Asn Val Glu Lys Trp Met Glu Lys Leu Glu Glu Ser
            275                 280                 285

Glu Ile Lys Lys Lys Leu Ser Ile Lys Thr Gly Leu Val Ala Val Ser
290                 295                 300

Leu Ser Val Gly Tyr Leu Trp Tyr Glu Cys Ile Tyr Lys Leu Asp Lys
305                 310                 315                 320

Val Ser Tyr Asn Lys Tyr His Pro Tyr Thr Ser Trp Ile Pro Ile Thr
                325                 330                 335

Val Tyr Ile Cys Leu Arg Asn Cys Thr Gln Gln Leu Arg Ser Phe Ser
                340                 345                 350

Leu Thr Leu Phe Ala Trp Leu Gly Lys Ile Thr Leu Glu Thr Tyr Ile
            355                 360                 365

Ser Gln Phe His Ile Trp Leu Arg Ser Asp Met Pro Asn Gly Gln Pro
            370                 375                 380

Lys Trp Leu Leu Ser Val Ile Pro Glu Tyr Pro Leu Leu Asn Phe Met
385                 390                 395                 400

Leu Thr Thr Ala Ile Tyr Val Leu Val Ser His Arg Leu Phe Glu Leu
                405                 410                 415

Thr Asn Thr Leu Lys Thr Val Phe Ile Pro Thr Lys Asp Asn Met Arg
                420                 425                 430

Leu Phe Tyr Asn Phe Val Ala Gly Ala Ala Ile Ser Leu Cys Leu Tyr
            435                 440                 445

Cys Val Ala Val Ile Leu Leu His Ile Leu His Ser Ala Val Ser Pro
            450                 455                 460

Ser Leu Val Leu Glu Asn Asn Met Val Ala Ser Asp Asp Leu Glu Leu
465                 470                 475                 480

Cys Ser

<210> SEQ ID NO 20
<211> LENGTH: 576
<212> TYPE: PRT
<213> ORGANISM: Artificial Sequence
<220> FEATURE:
<223> OTHER INFORMATION: partial P1_P._trichocarpa sequence from CAS1L
      gene family

<400> SEQUENCE: 20

| | | | | | | | | | | | | | | |
|---|---|---|---|---|---|---|---|---|---|---|---|---|---|---|
| Met | Phe | Ala | Met | Leu | Thr | Gly | Lys | Lys | Glu | Glu | Gly | Ile | Gly | Gly |
| 1 | | | | 5 | | | | | 10 | | | | | 15 |
| Pro | Lys | Glu | His | Trp | Val | Asp | Ala | Ser | Met | Pro | Met | Leu | Ser | Pro | Val |
| | | | 20 | | | | | 25 | | | | | 30 | | |
| Thr | Pro | Gly | Gln | Phe | Ser | Phe | Leu | Leu | Gly | Ile | Val | Pro | Val | Phe | Ala |
| | | | 35 | | | | | 40 | | | | | 45 | | |
| Ala | Trp | Ile | Tyr | Thr | Glu | Tyr | Leu | Glu | Tyr | Lys | Lys | Asn | Asn | Thr | Leu |
| | | 50 | | | | | 55 | | | | | 60 | | | |
| Ala | Lys | Ala | His | Ser | Asp | Val | Gly | Leu | Val | Glu | Leu | Gly | Asn | Glu | Ala |
| 65 | | | | | 70 | | | | | 75 | | | | | 80 |
| Val | Lys | Glu | Asp | Asp | Arg | Ala | Val | Leu | Leu | Glu | Gly | Val | Gln | Ser |
| | | | | 85 | | | | | 90 | | | | | 95 |
| Ala | Ser | Pro | Lys | Ala | Arg | Ser | Ser | Thr | Ser | Thr | Phe | Pro | Ile | Phe | Arg |
| | | | 100 | | | | | 105 | | | | | 110 | | |
| Phe | Phe | Thr | Met | Glu | Glu | Gln | Phe | Leu | Ile | Asp | Asn | Arg | Leu | Thr | Leu |
| | | | 115 | | | | | 120 | | | | | 125 | | |
| Arg | Ala | Ile | Ser | Glu | Phe | Gly | Phe | Phe | Met | Val | Tyr | Phe | Tyr | Ile | Cys |
| | 130 | | | | | 135 | | | | | 140 | | | | |
| Asp | Arg | Thr | Asp | Ile | Leu | Gly | Ser | Ser | Lys | Lys | Ser | Tyr | Asn | Arg | Asp |
| 145 | | | | | 150 | | | | | 155 | | | | | 160 |
| Leu | Phe | Leu | Phe | Leu | Tyr | Phe | Leu | Leu | Ile | Ile | Val | Ser | Ala | Ile | Thr |
| | | | | 165 | | | | | 170 | | | | | 175 | |
| Ser | Phe | Lys | Ile | His | His | Asp | Lys | Ser | Pro | Phe | Ser | Gly | Lys | Pro | Ile |
| | | | 180 | | | | | 185 | | | | | 190 | | |
| Leu | Tyr | Leu | Asn | Arg | His | Gln | Thr | Glu | Glu | Trp | Lys | Gly | Trp | Met | Gln |
| | | | 195 | | | | | 200 | | | | | 205 | | |
| Val | Leu | Phe | Leu | Met | Tyr | His | Tyr | Phe | Ala | Ala | Thr | Glu | Phe | Tyr | Asn |
| | 210 | | | | | 215 | | | | | 220 | | | | |
| Ala | Ile | Arg | Val | Phe | Ile | Ala | Ser | Tyr | Val | Trp | Met | Thr | Gly | Phe | Gly |
| 225 | | | | | 230 | | | | | 235 | | | | | 240 |
| Asn | Phe | Ser | Tyr | Tyr | Tyr | Val | Arg | Lys | Asp | Phe | Ser | Leu | Ala | Arg | Phe |
| | | | | 245 | | | | | 250 | | | | | 255 | |
| Ala | Gln | Met | Met | Trp | Arg | Leu | Asn | Phe | Leu | Val | Leu | Val | Cys | Cys | Val |
| | | | 260 | | | | | 265 | | | | | 270 | | |
| Val | Leu | Asn | Asn | Ser | Tyr | Met | Leu | Tyr | Ile | Cys | Pro | Met | His | Thr |
| | | | 275 | | | | | 280 | | | | | 285 | | |
| Leu | Phe | Thr | Leu | Met | Val | Tyr | Ala | Ala | Leu | Gly | Ile | Phe | Asn | Lys | Tyr |
| | | | 290 | | | | | 295 | | | | | 300 | | |
| Asn | Glu | Ile | Gly | Ser | Val | Met | Ala | Ala | Lys | Ile | Ala | Cys | Phe | Leu |
| 305 | | | | | 310 | | | | | 315 | | | | | 320 |
| Val | Val | Ile | Leu | Met | Trp | Glu | Ile | Pro | Gly | Val | Phe | Glu | Val | Trp |
| | | | | 325 | | | | | 330 | | | | | 335 |
| Ser | Pro | Phe | Thr | Phe | Leu | Phe | Gly | Tyr | Thr | Asp | Pro | Ala | Lys | Pro | Asp |
| | | | 340 | | | | | 345 | | | | | 350 | | |

```
Leu Pro Arg Leu His Glu Trp His Phe Arg Ser Gly Leu Asp Arg Tyr
            355                 360                 365

Ile Trp Ile Val Gly Met Ile Tyr Ala Tyr Tyr His Pro Met Val Glu
        370                 375                 380

Gly Trp Met Glu Lys Leu Glu Glu Thr Glu Ala Lys Arg Arg Ile Ser
385                 390                 395                 400

Ile Lys Thr Ala Val Ala Thr Ile Ser Leu Ala Val Gly Tyr Met Trp
                405                 410                 415

Tyr Glu Tyr Ile Tyr Lys Leu Asp Lys Cys Val His Leu Phe Glu Lys
            420                 425                 430

Cys His Pro Ala Leu Pro Leu Leu Gln Leu Asp Pro Phe Arg Leu Asn
        435                 440                 445

His Leu Leu Glu Ala Leu Ile Gly Gly Asn Leu Arg Glu Leu Leu Phe
    450                 455                 460

Leu Trp Leu Gly Lys Ile Thr Leu Glu Thr Tyr Ile Ser Gln Ile His
465                 470                 475                 480

Ile Trp Leu Arg Ser Gly Ile Pro Asp Gly Gln Pro Lys Leu Leu Leu
                485                 490                 495

Ser Leu Ile Pro Asp Tyr Pro Met Leu Asn Phe Met Leu Thr Thr Ser
            500                 505                 510

Ile Tyr Val Ala Val Ser Tyr Arg Leu Phe Asp Leu Thr Asn Thr Leu
        515                 520                 525

Lys Thr Ala Phe Val Pro Ser Lys Asp Asp Lys Arg Leu Thr Asn Asn
    530                 535                 540

Ile Ile Thr Ala Val Ala Val Ser Ile Val Leu Tyr Ser Leu Ser Phe
545                 550                 555                 560

Val Phe Leu Lys Ala Pro Gln Met Leu Val Leu Thr Ile Arg Thr Asp
                565                 570                 575

<210> SEQ ID NO 21
<211> LENGTH: 447
<212> TYPE: PRT
<213> ORGANISM: Artificial Sequence
<220> FEATURE:
<223> OTHER INFORMATION: partial P4_P._trichocarpa sequence from CAS1L
      gene family

<400> SEQUENCE: 21

Gly Leu Gln Pro Ala Ser Pro Lys Ala Arg Thr Pro Thr Ser Ser Phe
1               5                   10                  15

Pro Ile Phe Arg Phe Leu Met Met Glu Glu Gln Phe Leu Ile Asp Asn
            20                  25                  30

Arg Leu Thr Leu Arg Ala Ile Leu Glu Phe Gly Phe Phe Met Ala Tyr
        35                  40                  45

Phe Tyr Ile Cys Asp Arg Thr Asp Met Leu Gly Ser Ser Lys Lys Ser
    50                  55                  60

Tyr Asn Arg Asp Leu Phe Leu Phe Leu Tyr Phe Leu Leu Ile Ile Val
65                  70                  75                  80

Ser Ala Val Thr Ser Phe Thr Ile His His Asp Lys Ser Pro Phe Ser
                85                  90                  95

Gly Lys Pro Ile Leu Tyr Leu Asn Arg His Gln Thr Glu Glu Trp Lys
            100                 105                 110

Gly Trp Met Gln Val Leu Phe Leu Met Tyr His Tyr Phe Ala Ala Thr
        115                 120                 125

Glu Ile Tyr Asn Ala Ile Arg Met Phe Ile Ala Ala Tyr Val Trp Met
    130                 135                 140
```

```
Thr Gly Phe Gly Asn Phe Ser Tyr Tyr Tyr Val Arg Lys Asp Phe Ser
145                 150                 155                 160

Leu Ala Arg Phe Ala Gln Met Met Trp Arg Leu Asn Phe Leu Val Leu
            165                 170                 175

Phe Cys Cys Val Val Leu Asp Asn Ser Tyr Met Leu Tyr Tyr Ile Cys
                180                 185                 190

Pro Met His Thr Leu Phe Thr Leu Met Val Tyr Ala Ala Pro Ala Lys
            195                 200                 205

Pro Asp Leu Pro Arg Leu His Glu Trp His Phe Arg Ser Gly Leu Asp
210                 215                 220

Arg Tyr Ile Trp Ile Ile Gly Met Ile Tyr Ala Tyr Tyr His Pro Lys
225                 230                 235                 240

Val Glu Gly Trp Met Glu Lys Leu Glu Glu Thr Glu Ala Lys Arg Arg
                245                 250                 255

Ile Pro Ile Lys Thr Ala Val Ala Thr Ile Ser Leu Ala Val Gly Tyr
            260                 265                 270

Thr Trp Tyr Glu Tyr Ile Tyr Lys Leu Asp Lys Ile Ser Tyr Asn Lys
            275                 280                 285

Tyr His Pro Tyr Thr Ser Trp Ile Pro Ile Thr Val Tyr Ile Cys Leu
            290                 295                 300

Arg Asn Val Thr Gln Gln Phe Arg Cys Tyr Ser Leu Thr Leu Phe Ala
305                 310                 315                 320

Trp Leu Gly Lys Ile Thr Leu Glu Thr Tyr Ile Ser Gln Ile His Ile
                325                 330                 335

Trp Leu Arg Ser Gly Ile Pro Asp Gly Gln Pro Lys Leu Leu Leu Ser
                340                 345                 350

Leu Ile Pro Asp Tyr Pro Met Leu Asn Phe Met Leu Thr Thr Ser Ile
            355                 360                 365

Tyr Ile Gly Val Ser Tyr Arg Leu Phe Asp Leu Thr Asn Thr Leu Lys
370                 375                 380

Thr Ala Phe Val Pro Ser Lys Asp Asn Lys Arg Leu Thr Asn Asn Ile
385                 390                 395                 400

Ile Thr Ala Ala Ala Val Ser Ser Val Leu Tyr Ser Leu Ser Phe Val
                405                 410                 415

Phe Leu Lys Val Pro Gln Met Leu Ile Asn Asp Asn Leu Cys Ala Val
                420                 425                 430

Cys His Leu Asn Ala Gln Phe Ala Asp Thr Leu Asn Leu Gln Val
            435                 440                 445

<210> SEQ ID NO 22
<211> LENGTH: 542
<212> TYPE: PRT
<213> ORGANISM: Artificial Sequence
<220> FEATURE:
<223> OTHER INFORMATION: partial Selaginella_estExt_Genewise1.C sequence
      from CAS1L gene family

<400> SEQUENCE: 22

Met Val Glu Ile Ser Pro Pro Thr Thr Gly Gln Val Ala Leu Val Leu
1               5                   10                  15

Gly Phe Ile Pro Val Leu Thr Ala Trp Leu Tyr Ser Glu Phe Leu Glu
            20                  25                  30

Tyr Arg Lys Gln Pro Val Pro Gly Lys Ala His Ser Asp Ile Asn Leu
        35                  40                  45

Ser Glu Leu Glu His Gly Pro Arg Arg Asp Asn Glu Lys Asp Ser Leu
```

```
              50                  55                  60
Leu Glu Asn Gly Phe Ser Val Ser Gly Thr Leu Lys Gly Ser Phe Ser
 65                  70                  75                  80

Ile Arg Met Gln Leu Phe Lys Phe Phe Thr Leu Asn Glu Thr Phe Leu
                 85                  90                  95

Val Glu Asn Arg Ser Leu Leu Arg Ala Ile Ala Glu Phe Gly Cys Leu
                100                 105                 110

Leu Cys Tyr Phe Tyr Ile Cys Asp Arg Thr Asn Val Phe Gly Glu Leu
                115                 120                 125

Lys Lys Asn Tyr Ser Arg Asp Leu Phe Val Phe Leu Tyr Phe Leu Leu
                130                 135                 140

Ile Ile Val Ser Ser Ile Thr Ser Leu Lys Lys His Ala Glu Lys Ser
145                 150                 155                 160

Val Ala Ser Gly Lys Ser Ile Leu Tyr Leu Asn Arg His Gln Thr Glu
                165                 170                 175

Glu Trp Lys Gly Trp Met Gln Val Leu Phe Leu Met Tyr His Tyr Phe
                180                 185                 190

Ala Ala Ala Glu Ile Tyr Asn Ala Ile Arg Leu Phe Ile Ala Gly Tyr
                195                 200                 205

Val Trp Met Thr Gly Phe Gly Asn Phe Ser Tyr Tyr Tyr Val Arg Lys
210                 215                 220

Asp Phe Ser Leu Gly Arg Phe Ala Gln Met Met Trp Arg Leu Asn Phe
225                 230                 235                 240

Leu Val Thr Phe Cys Cys Ile Val Leu Asn Asn Ser Tyr Met Leu Tyr
                245                 250                 255

Tyr Ile Cys Pro Met His Thr Leu Phe Thr Leu Met Val Tyr Cys Ser
                260                 265                 270

Leu Gly Ile Leu Asn Lys Tyr Asn Glu Val Pro Ser Val Ile Gly Ala
                275                 280                 285

Lys Ile Ala Ala Cys Phe Ala Val Val Ile Leu Val Trp Glu Val Pro
290                 295                 300

Gly Val Phe Asp Phe Val Trp Arg Pro Phe Thr Phe Leu Val Glu Tyr
305                 310                 315                 320

Thr Asp Pro Gly Lys Pro Asp Leu Pro Val Leu His Glu Trp His Phe
                325                 330                 335

Arg Ser Gly Leu Asp Arg Tyr Ile Trp Ile Tyr Gly Met Ile Cys Ala
                340                 345                 350

Tyr Phe His Pro Thr Val Glu Arg Trp Leu Glu Lys Leu Glu Glu Leu
                355                 360                 365

Glu Cys Arg Arg Lys Phe Thr Tyr Lys Ser Val Ile Val Phe Val Ala
370                 375                 380

Ser Leu Val Gly Tyr Leu Trp Tyr Val His Ile Tyr Lys Leu Asp Lys
385                 390                 395                 400

Leu Ser Tyr Asn Lys Leu His Pro Tyr Thr Ser Trp Ile Pro Ile Ser
                405                 410                 415

Val Tyr Ile Val Leu Arg Asn Val Ser Gln Pro Leu Arg Asn Trp Ser
                420                 425                 430

Leu Thr Leu Phe Ala Trp Leu Gly Lys Ile Thr Leu Glu Thr Tyr Ile
                435                 440                 445

Ala Gln Phe His Ile Trp Leu Arg Thr Gly Val Ser Asn Gly Gln Pro
                450                 455                 460

Lys Leu Leu Leu Ser Phe Ile Pro Asp Tyr Pro Met Leu Asn Phe Met
465                 470                 475                 480
```

```
Leu Ala Thr Ser Ile Tyr Ile Leu Val Ser Tyr Arg Leu Phe Glu Leu
            485                 490                 495

Thr Asn Thr Leu Lys Ser Ala Phe Val Pro Asn Lys Asp Asn Asn Arg
            500                 505                 510

Leu Phe Leu Met Val Val Ser Gly Gly Thr Ile Phe Ser Leu Leu Tyr
        515                 520                 525

Gly Val Ser Tyr Leu Leu Val Lys Ile Pro Tyr Ile Leu Val
        530                 535                 540
```

METHOD OF REDUCING ACETYLATION IN PLANTS TO IMPROVE BIOFUEL PRODUCTION

CROSS-REFERENCE TO RELATED APPLICATIONS

This application is a continuation of U.S. application Ser. No. 13/201,851, filed Sep. 15, 2011, which is a U.S. National Phase entry under 35 U.S.C. § 371 of International Application No. PCT/US2010/024477, filed Feb. 17, 2010, which claims priority benefit of U.S. provisional patent application No. 61/153,202, filed Feb. 17, 2009, each of which applications are herein incorporated by reference in their entirety for all purposes.

STATEMENT AS TO RIGHTS TO INVENTIONS MADE UNDER FEDERALLY SPONSORED RESEARCH AND DEVELOPMENT

The invention described and claimed herein was made using funds supplied by the U.S. Department of Energy under Contract No. DE-ACO2-05CH11231. The government has certain rights in this invention.

REFERENCE TO SUBMISSION OF A SEQUENCE LISTING AS AN ASCII TEXT FILE

This application includes a Sequence Listing as a text file created on Feb. 3, 2017 named 077429_1018267_SEQ_LST_ST25" and containing 73,432 bytes. The material contained in this text file is hereby incorporated by reference in its entirety for all purposes.

BACKGROUND OF THE INVENTION

Biomass for biofuel production contains large amounts of xylan as well as smaller amounts of other matrix polysaccharides, such as xyloglucan, mannans, pectins, and the like. Efficient biofuel production requires efficient degradation of these polysaccharides. Enzymatic degradation into monosaccharides is hindered, however, by acetyl ester substitutions on the polysaccharide backbone. The inhibition of degradation by acetyl esters can be significant, as substitution can be at a high level, e.g., typically 25-50% of the xylose residues of grass xylans are acetylated. Moreover, the acetic acid that is released during enzymatic or chemical degradation is inhibitory to organisms, such as yeast, that are used for fermentation. The acetic acid contained in a biomass mixture for fermentation can easily be in the order of 0.1 M or 6 g/l, which is a highly inhibitory level. Reduction in the level of acetic acid would therefore be highly beneficial for fermentation. Accordingly, there is a need for improvement to biofuel production to reduce acetic acid levels.

A pathogenic fungus, *Cryptococcus neoformans*, has a polysaccharide coat consisting of O-acetylated glucuronoxylomannans. A protein encoded by the Cas1p gene has been identified as being essential for acetylation of the coat polysaccharide (Janbon et al., *Molec. Microbiol.* 42:453-467, 2001). Although the gene has been putatively annotated as an acetyltranserase, its biochemical activity was not confirmed. Homologs of this gene have been identified in various plants.

The present invention is based, in part, on the discovery that mutations in homologs to Cas1p reduce polysaccharide acetylation. Plants having reduced polysaccharide acetylation in accordance with the present invention can be used, for example, to provide plant mass that produces lower levels of acetic acid during fermentation.

BRIEF SUMMARY OF THE INVENTION

The invention provides, in part, methods of engineering plants to reduce the level of acetylation in plants, plants that have been engineered in accordance with the methods and methods of using such plants, e.g., to improve the yield for biofuel production. Thus, in one aspect, the invention provides a method of improve the yield of a fermentation reaction from an enzymatic or chemical degradation of acetylated products in a reaction comprising plant material, e.g., cell wall material, the method comprising providing a plant that has been engineered to decrease the activity of at least one CAS1L gene, e.g., a CAS1L1 or CAS1L2 gene, in the plant; and incubating the plant material in the reaction. The plants can be engineered to decrease the activity of at least two CAS1L genes, or to decrease the activity of at least three CAS1L genes. In some embodiments, a plant can be engineered to reduce the activity of four CAS1L genes.

In some embodiments, improvement in yield can be an improvement of the final yield from, or efficiency of, a fermentation reaction, wherein the method comprises: enzymatically or chemically degrading plant material from a mutant CAS1L plant that has decreased activity of at least one CAS1L gene to obtain degradation products; and fermenting the degradation products in a fermentation reaction, wherein the final yield, or efficiency of, the fermentation reaction is increased relative to the final yield, or efficiency, of a fermentation reaction using corresponding plant material from a wildtype CAS1L plant. In some embodiment, the steps of degrading the plant material and fermenting the degradation products occur in the same reaction mixture. Alternatively, the steps of degrading the plant material and fermenting the degradation products can occur in separate reaction mixtures. In some embodiments, the improvement of the efficiency of the fermentation reaction is an increase in the amount of product obtained per unit enzyme over a period of time compared to the amount of product obtained using corresponding plant material from a wildtype CAS1L plant per unit enzyme over the same period of time. In some embodiments, the mutant CAS1L plant has been engineered to decrease the activity of at least one CAS1L gene, e.g., a CAS1L1 or a CAS1L2 gene. In some embodiments, the plants are engineered to decrease the activity of at least two CAS1L genes, or to decrease the activity of at least three CAS1L genes. In some embodiments, a plant can be engineered to reduce the activity of four CAS1L genes.

In some embodiments, the invention provides a method of chemically degrading or enzymatically degrading plant material from a mutant CAS1L plant that has decreased activity of at least one CAS1L gene to obtain degradation products for a fermentation reaction, wherein the amount of degradation product obtained and/or the efficiency of the degradation reaction is improved compared to a corresponding reaction in which wildtype CAS1L plant material is employed. In some embodiments, the degradation reaction is an enzymatic reaction and the efficiency (e.g., amount of product obtained per unit enzyme per unit of time) of the degradation reaction is improved. In some embodiments, the mutant CAS1L plant has been engineered to decrease the activity of at least one CAS1L gene, e.g., a CAS1L1 or a CAS1L2 gene. In some embodiments, the plants are engineered to decrease the activity of at least two CAS1L genes, or to decrease the activity of at least three CAS1L genes. In some embodiments, a plant can be engineered to reduce the activity of four CAS1L genes.

In some embodiments, the plant is a transgenic plant that comprises a vector comprising a nucleic acid sequence that encodes an RNAi, e.g., an artificial microRNA (miRNA) or other nucleic acid that encodes an RNAi, that inhibits expression of at least one CAS1L gene.

In some embodiments, the plants that is engineered in accordance with the invention is selected from the group consisting of corn, sorghum, millet, *miscanthus*, sugarcane, poplar, pine, *eucalyptus*, wheat, rice, soy, cotton, barley, switchgrass, turfgrass, ryegrass, bahiagrass, bermudagrass, dallisgrass, pangolagrass, big bluestem, Indian grass, fescue, *Dactylis* sp. Brachypodium, smooth bromegrass, orchardgrass, Kentucky bluegrass, timothy, *Kochia*, forage soybeans, alfalfa, clover, hemp, kenaf, tobacco, potato, bamboo, rape, sugar beet, sunflower, willow, and *eucalyptus*.

In an additional aspect, the invention provides a plant comprising a vector that comprises an RNAi that inhibits a CAS1L gene. In some embodiments, the plants is selected from the group consisting of corn, sorghum, millet, *miscanthus*, sugarcane, poplar, pine, *eucalyptus*, wheat, rice, soy, cotton, barley, switchgrass, turfgrass, ryegrass, bahiagrass, bermudagrass, dallisgrass, pangolagrass, big bluestem, Indian grass, fescue, *Dactylis* sp. Brachypodium, smooth bromegrass, orchardgrass, Kentucky bluegrass, timothy, *Kochia*, forage soybeans, alfalfa, clover, hemp, kenaf, tobacco, potato, bamboo, rape, sugar beet, sunflower, willow, and *eucalyptus*.

The invention also provides an isolated mutant CAS1L plant in which at least two CAS1L genes are inhibited. In some embodiments, three or four CAS1L genes are inhibited. In some embodiments, the plant is selected from the group consisting of corn, sorghum, millet, *miscanthus*, sugarcane, poplar, pine, *eucalyptus*, wheat, rice, soy, cotton, barley, switchgrass, turfgrass, ryegrass, bahiagrass, bermudagrass, dallisgrass, pangolagrass, big bluestem, Indian grass, fescue, *Dactylis* sp. Brachypodium, smooth bromegrass, orchardgrass, Kentucky bluegrass, timothy, *Kochia*, forage soybeans, alfalfa, clover, hemp, kenaf, tobacco, potato, bamboo, rape, sugar beet, sunflower, willow, and *eucalyptus*.

In some embodiments, the invention also provides a method of producing a plant that has reduced acetylation in the cell wall material, the method comprising inhibiting expression of at least one CAS1L gene in the plant using RNAi. In some embodiments, the method further comprises determining the level of acetylation in the cell wall of the plant.

In another aspect, the invention provides bulk harvested material comprising material from at least two engineered plants, e.g., grass plants, that have decreased expression of at least one CAS1L gene. In some embodiments, the bulk harvested material is present in a fermentation reaction.

In an additional aspect, the invention provides a plant, e.g., a grass, engineered to have reduced expression of at least one CAS1L gene, wherein the plant has at least a 10% reduction in cell wall acetylation in comparison to a plant that has not been engineered.

The invention further provides a polysaccharide or polysaccharide fraction, e.g., homogalacturonan or pectin, isolated from a plant that has at least a 10% reduction in cell wall acetylation in comparison to a wildtype plant. In some embodiment, the invention provides a food ingredient containing such a polysaccharide.

BRIEF DESCRIPTION OF THE DRAWINGS

FIG. 1 provides an alignment of plant CAS1L genes: P2_P._trichocarpa (SEQ ID NO:18), P3_P._trichocarpa (SEQ ID NO: 19), Cas1L3_AT2G34410 (SEQ ID NO:3), Cas1L4_AT1G29890 (SEQ ID NO:4), Cas1L1_AT5G46340 (SEQ ID NO:1), Os01g0631100_Oryza (SEQ ID NO:15), Os05g0582100_Oryza (SEQ ID NO:16), Os03g0314200_Oryza (SEQ ID NO:17)), Selaginella_estExt Genewisel.C (SEQ ID NO:22), P1_P._trichocarpa (SEQ ID NO: 20), P4_P._trichocarpa (SEQ ID NO: 21), and Cas1L2_AT3G06550 (SEQ ID NO:5).

DETAILED DESCRIPTION OF THE INVENTION

Figure 2:
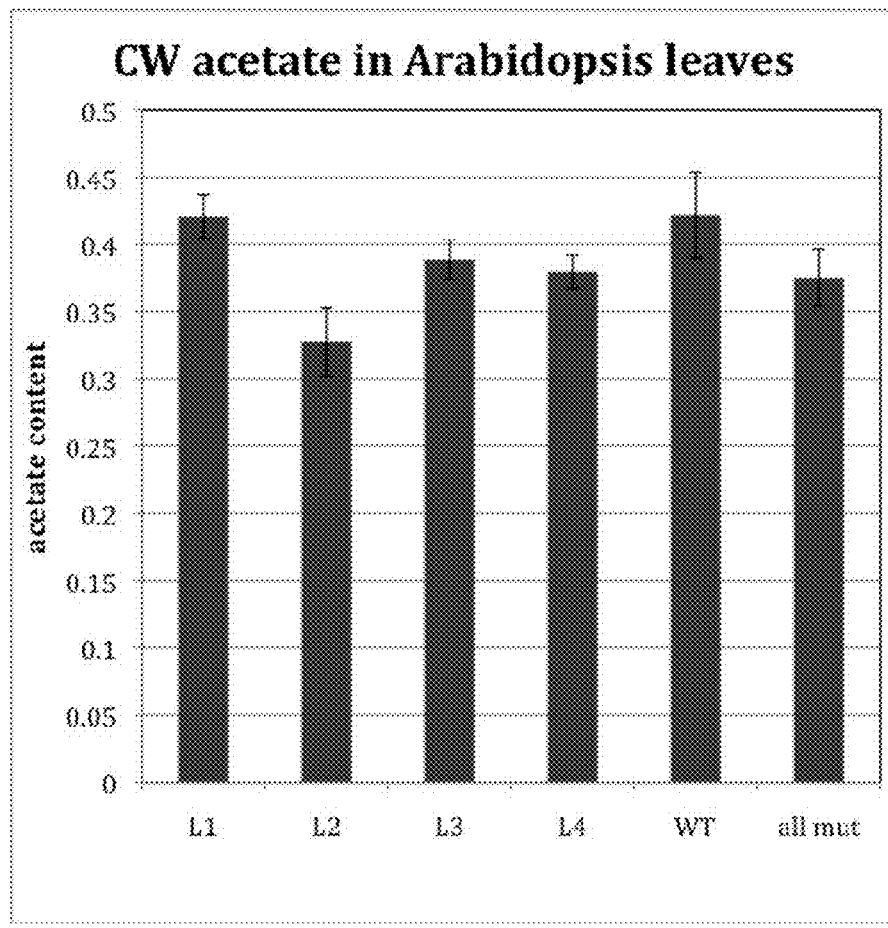
FIG. 2 shows acetate levels in a small number of *Arabidopsis* plants that have been engineered to reduce CAS1L gene expression.

The term "biomass" in the context of this application refers to plant material that is processed to provide a product, e.g., a biofuel such as ethanol, or livestock feed. Such plant material can include whole plants, or parts of plants, e.g., stems, leaves, branches, shoots, roots, tubers, and the like.

The term "acetate" as used herein is used to refer to acetyl esters bound to polysaccharides and glycan structures on glycoproteins and proteoglycans. The acetyl ester can be bound to different OH-groups on sugars, and individual sugar residues can contain more than one acetyl ester group. Many different plant polysaccharides are known to be acetylated, including xylan, mannan, xyloglucan, and pectin.

A "fermentation reaction" as used herein is used to refer to the conversion of a substrate into a product, typically by an enzymatic reaction. Such reactions in the context of this invention can be anaerobic or aerobic. Typically, a fermentation reaction used in this invention is an anaerobic reaction in which yeast or bacteria convert polysaccharides, oligosaccharides and/or sugars to alcohols, acids, hydrocarbons and/or esters.

In the context of this invention, the term "yield", when referring to an enzymatic or chemical reaction for the conversion of a substrate into a product, refers to efficiency as well as overall amount of the product. Thus, the term "improved yield" not only refers to increases in overall, or final, yield of a reaction (i.e., the amount of product obtained per amount of starting material), but also includes a faster reaction rate that increases the amount of product produced over a shorter period when using biomass from a mutant CAS1L plant in comparison to corresponding biomass from the wildtype plant. In some embodiments in which CAS1L mutant plant material is degraded in an enzymatic reaction, "improved yield" includes an increase in the amount of product obtained per enzyme unit over a defined unit of time in comparison to the yield obtained using wildtype CAS1L plant material.

In the context of this invention "corresponding plant material from a wildtype CAS1L plant" refers to plant material that is from the same part of the plant as the CAS1L mutant plant material. As understood in the art, improved yield is based upon comparisons of the same amount of corresponding plant material.

A plant that has a "mutant CAS1L gene" in the context of this invention refers to a plant in which at least the CAS1L gene is inactivated, or mutated to reduce expression, relative to a plant with a wildtype CAS1L gene.

A plant that has been "engineered to have decreased expression of a CAS1L gene" refers to a plant that has been modified by mutagenesis, and/or genetic engineering, e.g., engineering to express RNAi that targets one or more CAS1L genes, to exhibit decreased expression of the targeted CAS1L gene or genes.

A "CAS1L gene" refers generally to a nucleic acid encoding a polypeptide that is a member of the CAS1L gene family. Examples of members of the CAS1L gene family include CAS1L1, CAS1L2, CAS1L3, and CAS1L4. In the context of this invention, a CAS1L polypeptide that is encoded by a CAS1L gene has substantial identity to a polypeptide comprising the sequence set forth in SEQ ID NO:1, SEQ ID NO:2, SEQ ID NO:3, SEQ ID NO:4, or SEQ ID NO:5; or to a CAS1L gene sequence set forth in FIG. 1. A "CAS1L gene" is also referred to herein as an RWA gene. Thus, for example, CAS1L genes CAS1L1, CAS1L2, CAS1L3, and CAS1L4 are also referred to as RWA1, RWA2, RWA3 and RWA4 genes.

The terms "decreased expression", "reduced expression", or "inhibited expression" of a CAS1L gene refers to a reduction in the level of expression of the CAS1L gene in an engineered plant compared to the level of expression in a wildtype plant. Thus, decreased expression can be a reduction in expression of a CAS1L gene of 10%, 20%, 30%, 40%, 50%, 60%, 70%, 80%, or 90% or greater. Decreased expression can be assessed by measuring decreases in the level of RNA encoded by the gene and/or decreases in the level of CAS1L protein or protein activity. CAS1L protein/protein activity can be assessed directly or indirectly, e.g., by measuring an endpoint such as the acetate content of a part of plant in which the CAS1L gene is expressed.

The phrase "substantially identical," in the context of two nucleic acids or polypeptides, refers to a sequence or subsequence that has at least 50% identity, typically at least 60% sequence identity, to a reference sequence. Percent identity can be any integer from 50% to 100%. In some embodiments, a sequence is at least 60%, 65%, 70%, 75%, 80%, 85%, 90%, 95%, or 99% identical when compared to a reference sequence.

In the case of both expression of transgenes and inhibition of endogenous genes (e.g., by antisense, or sense suppression) one of skill will recognize that the inserted polynucleotide sequence need not be perfectly identical and may be "substantially identical" to a sequence of the gene from which it was derived. In the case of polynucleotides used to inhibit expression of an endogenous gene, the introduced sequence need not be perfectly identical to a sequence of the target endogenous gene. The introduced polynucleotide sequence will typically be at least substantially identical (as determined below) to the target endogenous sequence. Thus, an introduced "polynucleotide sequence from" a CAS1L gene may not be identical to the target CAS1L gene to be suppressed, but is functional in that it is capable of inhibiting expression of the target CAS1L gene. As explained below, these variants are specifically covered by this term.

The phrase "at least one CAS1L gene, or "at least two CAS1L genes", or "at least three CAS1L genes" is used to refer to members of the CAS1L gene family in a plant that has multiple CAS1L genes. For example, in the alignment in FIG. 1, rice has three CAS1L gene family members (Os01g0631100_Oryza (SEQ ID NO:15), Os05g0582100_Oryza (SEQ ID NO:16), and Os03g0314200_Oryza (SEQ ID NO:17)), poplar has four CAS1L gene family members (P2_P._trichocarpa (SEQ ID NO: 18), P3_P._trichocarpa (SEQ ID NO: 19), P1_P._trichocarpa (SEQ ID NO: 20), and P4_P._trichocarpa (SEQ ID NO: 21)), and *Arabidopsis* has four CAS1L gene family members (SEQ ID NOs: 3, 4, 1, and 5).

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman Add. *APL. Math.* 2:482 (1981), by the homology alignment algorithm of Needle man and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection. In some embodiments, percent identity is determined using the BLAST2 algorithm set at the default settings.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. A "comparison window" may be, e.g., 20, 50, 100, 400, or more nucleotides ore amino acids in length; or may be the entire length of the sequences being compared.

Proteins that are substantially identical include those that have conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For example, stringent conditions for hybridization, such as RNA-DNA hybridizations in a blotting technique are those which include at least one wash in 0.2×SSC at 55° C. for 20 minutes, or equivalent conditions.

A CAS1L polynucleotide sequence for use in the invention can also be amplified using PCR techniques, e.g., primers that are designed to amplify nucleic acid sequences that encode CAS1L protein sequences set forth in SEQ ID NOs: 1, 2, 3, 4, or 5.

The term "plant", as used herein, can refer to a whole plant or parts plant parts e.g., cuttings, tubers, pollen, leaves, stems, flowers, roots, fruits, branches, and the like. The term also encompasses individual plant cells, groups of plant cells (e.g., cultured plant cells), protoplasts, plant extracts, seeds, and progeny thereof. The term includes plants of a variety of a ploidy levels, including polyploid, diploid and haploid.

The term "progeny" refers generally to the offspring of a cross, and includes direct F1 progeny, as well as later generations of F2, F3, etc.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants.

An "expression cassette" refers to a nucleic acid construct, which when introduced into a host cell, results in transcription and/or translation of a RNA or polypeptide, respectively.

The term "isolated", when applied to a nucleic acid or protein, denotes that the nucleic acid or protein is essentially free of other cellular components with which it is associated in the natural state. It is preferably in a homogeneous state and may be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest.

The term "bulk harvested material" refers to combined plant material harvested from at least three plants, preferably at least 5, 10, 25, 50, 100, 500, or 1000 or more plants. The plant material may be whole plants, or parts of the plants, e.g., leaves or stems harvested from the plants. In some embodiments, the plant material present in the bulk harvested material is crushed or milled to a desired particle size, e.g., a size that is useful for producing biofuel.

Introduction

This invention is based, in part, on the discovery that plants can be engineered to suppress CAS1L gene expression to reduce the amount of acetate, i.e., polymer-bound acetyl esters, present in the plant material, thereby enhancing yield in an enzymatic reaction, e.g., a fermentation reaction, to obtain a desired product. Often, the product is a biofuel, such as ethanol. In typical embodiments, the fermentation reaction employs a microorganism, such as a yeast or bacteria, that is sensitive to acetic acid levels in the reaction.

In some embodiments, a plant such as a sugar beet or potato, that is engineered to reduce the amount of acetate in the plant material can be used as a source of other products, such as a pectin, that can be employed as a food ingredient.

The invention therefore provides methods of engineering plants to reduce acetate by suppressing expression of at least one, often two or three, CAS1L genes in the plant. The invention further provides plants that have been thusly engineered, as well as methods of using such plants, e.g., to enhance biofuel yield from plant material.

In the current invention, the yield of a fermentation reaction to obtain a desired product is increased due to the reduced acetylation in CAS1L mutant plants. This can be accomplished that by having less acetate in the products that are used in the fermentation. Either an enzymatic or chemical degradation can be used.

In some embodiments, an enzymatic degradation is employed. In such embodiments, the enzymatic degradation reaction can itself be improved due to the lowered acetate content in CAS1L mutant plants. Typically, this results in increased yield in a fermentation reaction (i.e., either in the rate of fermentation and/or the total amount of fermentation product generated).

In some embodiments, improved degradation can also be advantageous without an effect on the final yield in fermentation. For example, in some embodiments, a reaction may employ less enzyme in order to degrade the biomass obtained from CAS1L mutant plants compared to the amount of enzyme required to degrade the biomass from wildtype CAS1L plants. Accordingly, in some embodiments, improved yield from biomass from CAS1L mutant plants results from an increase in the amount of degradation product generated per enzyme unit per unit of time relative to the yield from corresponding biomass from a wildtype CAS1L plant.

In the current invention, the degradation and fermentation of the biomass from the plant can be performed in one reaction mixture or using separate reaction mixtures. Thus, plant material from a CAS1L mutant plant, e.g., cell wall material from shoots, stems, etc., can be degraded either enzymatically or chemically in one reaction and the degradation products then fermented in a separate reaction mixture. In other embodiments, the degradation reaction and the fermentation reaction are conducted in the same reaction mixture such that the degradation products generated from enzymatic or chemical degradation of the plant biomass is fermented in the same mixture in which the biomass is degraded.

An "improved yield" from a fermentation reaction can thus arise from an improvement in the overall amount of product obtained or from an increased efficiency of the overall reaction.

Plants that can be Engineered in Accordance with the Invention

Various kind of plants can be engineered to reduce CAS1L gene expression as described herein to reduce acetate levels. The plant may be a monocotyledonous plant or a dicotyledonous plant. In certain embodiments of the invention, plants are green field plants.

In other embodiments, plants are grown specifically for "biomass energy". For example, suitable plants include corn, switchgrass, sorghum, miscanthus, sugarcane, poplar, pine, wheat, rice, soy, cotton, barley, turf grass, tobacco, potato, bamboo, rape, sugar beet, sunflower, willow, and eucalyptus. In further embodiments, the plant is switchgrass (Panicum virgatum), giant reed (Arundo donax), reed canarygrass (Phalaris arundinacea), Miscanthus×giganteus, Miscanthus sp., sericea lespedeza (Lespedeza cuneata), millet, ryegrass (Lolium multiflorum, Lolium sp.), timothy, Kochia (Kochia scoparia), forage soybeans, alfalfa, clover, sunn hemp, kenaf, bahiagrass, bermudagrass, dallisgrass, pangolagrass, big bluestem, indiangrass, fescue (Festuca sp.), Dactylis sp., Brachypodium distachyon, smooth bromegrass, orchardgrass, or Kentucky bluegrass among others.

Inhibition of CAS1L Gene Expression

The invention employs various routine recombinant nucleic acid techniques. Generally, the nomenclature and the laboratory procedures in recombinant DNA technology described below are those well known and commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel et al., eds., 1994-1999, updated through 2008).

Acetyl-related protein has been identified in Cryptococcus neoformans, where mutation in the Cas1p gene leads to lack of acetylation of the coat polysaccharide (Janbon et al. Molecular Microbiology 42: 453-467, 2001). The protein therefore plays a role in acetylation and has been described as a putative acetyl transferase, although no transferase activity has been demonstrated. In the Genbank database, several homologs of the Cryptococcus protein are annotated as 'acetyl transferase', 'acetyl transferase-related', 'putative acetyl transferase' etc. These annotations are based on the sequence similarity with the Cryptococcus protein.

A CAS1L nucleic acid that is targeted for suppression (inhibition) in this invention encodes a CAS1L protein that is substantially similar to SEQ ID NO:1, 2, 3, 4, or 5, or a fragment thereof. CAS1L proteins that are substantially similar to SEQ ID NO:1, 2, 3, 4, or 5, or a fragment thereof, have one or more conserved domains. For example, FIG. 1 provides an alignment of plant CAS1L protein sequences, including sequences from Arabidopsis (SEQ ID NOs: 3, 4, 1 and 5), rice (SEQ ID NOs:15-17), poplar (SEQ ID NOs:18-21), and Selagninella (SEQ ID NO:22). These sequences include a highly conserved region, which is shown below using Arabidposis CAS1L2 as a reference sequence (SEQ ID NO:11):

YLNRHQTEEWKGWMQVLFLMYHYFAAAEYYNAIRVFIACYVWMTGFGNFS

YYYIRKDFSLARFAQMMWRLNFLVIFSCIVLNNSYMLYYICPMHTLFTLM

VY

This region is at least 78% conserved (i.e., in the context of this invention 78% identical to) Arabidopsis CAS1L2 in CAS1L sequences in FIG. 1. The following sequence provides examples of residue positions, designated by "X", that may vary in this conserved sequence (SEQ ID NO:12). In some embodiments, a residue occurring at an "X" position is a conservative amino acid substitution relative to the amino acid residue that occurs at that position in a CAS1L sequence shown in FIG. 1.

YLNRHQTEEWKGWMQVXFLMYHYFXAXEXYNAIRXFIAXYVWMTGFGNFS

YYYXXKDFSXXRFXQMMWRLNXXVXXXCXXLXNXYXLYYTCPMHTLFTXM

VY.

Accordingly, a CAS1L nucleic acid that is targeted for inhibition as described herein typically encodes a protein that contains a region that has at least 60%, 65%, 70%, or 75% or great identity to this sequence.

Another motif that is conserved is the sequence LHEWHFRSGLDRYIWI (SEQ ID NO:13). Accordingly, a CAS1L nucleic acid sequence that is targeted for inhibition typically encodes a protein that contains this motif.

Furthermore, a CAS1L nucleic acid typically encodes a protein that has substantial identity, e.g., at least 60%, 65%, 70%, or 75% identity to a central region, residues 116-350, shown with reference to an Arabidopsis CasL3 protein sequence (SEQ ID NO:14):

YFYISDRTSLLGESKKNYNRDLFLFLYCLLIIVSAMTSLKKHNDKSPIT

GKSILYLNRHQTEEWKGWMQVLFLMYHYFAAAEIYNAIRVFIAAYVWMT

GFGNFSYYYIRKDFSLARFTQMMWRLNLFVAFSCIILNNDYMLYYICPM

HTLFTLMVYGALGIFSRYNEIPSVMALKIASCFLVVIVMWEIPGVFEIF

WSPLTFLLGYTDPAKPELPLLHEWHFRSGLDRYIWIIGM.

A plant may express multiple CAS1L family members. For example, Arabidopsis has multiple CAS1L family members, which have a high degree of amino acid sequence identity. For example, CAS1L1, CAS1L3, and CAS1L4 have at least 68%, 69%, and 74% amino acid sequence identity to CAS1L2.

In the present invention, at least one CAS1L gene sequence is inhibited in a plant. For example, in some embodiments, one CAS1L gene is inhibited. Such a gene may encode a protein that has at least 50%, 55%, 60%, 65%, 70%, or 75% identity, or greater, to a CAS1L1 or CAS1L2 reference sequence, e.g., SEQ ID NO:1 or 2. In some embodiments, plants are generated in which at least two CAS1L genes are inhibited. Plants may also be engineered in which at least three CAS1L genes or four CAS1L genes are inhibited. As understood in the art, the number of CAS1L genes that are inhibited will depend on such factors as effects on plant growth, plant general health and the like.

In some embodiments, a CAS1L gene that is inhibited has a coding nucleic acid sequence that is substantially identical, e.g., at least 50%, 60%, 65%, 70%, or 75% identical, to the CAS1L nucleic acid sequences SEQ ID NO:6, 7, 8, 9, or 10. Of the CAS1L nucleic acid sequences shown in SEQ ID NOs. 6-10, the sequences have the following percent identity as determined by Blast using standard parameters:

|  | CAS1L1 | CAS1L2-a | CAS1L2-b | CAS1L3 | CAS1L4 |
| --- | --- | --- | --- | --- | --- |
| CAS1L1 |  |  |  |  |  |
| CAS1L2-a | 73 |  |  |  |  |
| CAS1L2-b | 73 | 99 |  |  |  |
| CAS1L3 | 76 | 71 | 71 |  |  |
| CAS1L4 | 77 | 72 | 72 | 87 |  |

Methods of Inhibiting CAS1L Gene Expression

The CAS1L gene can be suppressed using any number of techniques well known in the art. For example, one method of suppression is sense suppression (also known as co-suppression). Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279-289 (1990); Flavell, *Proc. Natl. Acad. Sci., USA* 91:3490-3496 (1994); Kooter and Mol, *Current Opin. Biol.* 4:166-171 (1993); and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity can exert a more effective repression of expression of the endogenous sequences. In some embodiments, sequences with substantially greater identity are used, e.g., at least about 80, at least about 95%, or 100% identity are used. As with antisense regulation, further discussed below, the effect can be designed and tested to apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. Furthermore, the introduced sequence need not have the same intron or exon pattern, and identity of non-coding segments will be equally effective. In some embodiments, a sequence of the size ranges noted above for antisense regulation is used, i.e., 30-40, or at least about 20, 50, 100, 200, 500 or more nucleotides.

Endogenous gene expression may also be suppressed by means of RNA interference (RNAi) (and indeed co-suppression can be considered a type of RNAi), which uses a double-stranded RNA having a sequence identical or similar to the sequence of the target gene. As used herein RNAi, includes the use of micro RNA, such as artificial miRNA to suppress expression of a gene.

RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementary RNAs or may be a single RNA with internally complementary sequences that form a double-stranded RNA. Although complete details of the mechanism of RNAi are still unknown, it is considered that the introduced double-stranded RNA is initially cleaved into small fragments, which then serve as indexes of the target gene in some manner, thereby degrading the target gene. RNAi is known to be also effective in plants (see, e.g., Chuang, C. F. & Meyerowitz, E. M., *Proc. Natl. Acad. Sci. USA* 97: 4985 (2000); Waterhouse et al., *Proc. Natl. Acad. Sci. USA* 95:13959-13964 (1998); Tabara et al. *Science* 282:430-431 (1998); Matthew, *Comp Funct Genom* 5: 240-244 (2004); Lu, et al., *Nucleic Acids Res.* 32(21):e171 (2004)).

Thus, in some embodiments, inhibition of a CAS1L gene is achieved using RNAi techniques. For example, to achieve suppression of the expression of a DNA encoding a protein using RNAi, a double-stranded RNA having the sequence of a DNA encoding the protein, or a substantially similar sequence thereof (including those engineered not to translate the protein) or fragment thereof, is introduced into a plant of interest. As used herein, RNAi and dsRNA both refer to gene-specific silencing that is induced by the introduction of a double-stranded RNA molecule, see e.g., U.S. Pat. Nos. 6,506,559 and 6,573,099, and includes reference to a molecule that has a region that is double-stranded, e.g., a short hairpin RNA molecule. The resulting plants may then be screened for a phenotype associated with the target CAS1L protein, e.g., reduced acetate, and/or by monitoring steady-state RNA levels for transcripts encoding the protein. Although the genes used for RNAi need not be completely identical to the target gene, they may be at least 70%, 80%, 90%, 95% or more identical to the target gene sequence. See, e.g., U.S. Patent Publication No. 2004/0029283. The constructs encoding an RNA molecule with a stem-loop structure that is unrelated to the target gene and that is positioned distally to a sequence specific for the gene of interest may also be used to inhibit target gene expression. See, e.g., U.S. Patent Publication No. 2003/0221211.

The RNAi polynucleotides may encompass the full-length target RNA or may correspond to a fragment of the target RNA. In some cases, the fragment will have fewer than 100, 200, 300, 400, or 500, nucleotides corresponding to the target sequence. In addition, in some embodiments, these fragments are at least, e.g., 50, 100, 150, 200, or more nucleotides in length. Interfering RNAs may be designed based on short duplexes (i.e., short regions of double-stranded sequences). Typically, the short duplex is at least about 15, 20, or 25-50 nucleotides in length (e.g., each complementary sequence of the double stranded RNA is 15-50 nucleotides in length), often about 20-30 nucleotides, e.g., 20, 21, 22, 23, 24, 25, 26, 27, 28, 29, or 30 nucleotides in length. In some cases, fragments for use in RNAi will be at least substantially similar to regions of a target protein that do not occur in other proteins in the organism or may be selected to have as little similarity to other organism transcripts as possible, e.g., selected by comparison to sequences in analyzing publicly-available sequence databases. Thus, RNAi fragments may be selected for similarity or identity with conserved domains of CAS1L sequences, such as those described herein, that lacking significant homology to sequences in the databases).

In some embodiments, an RNAi is introduced into a cell as part of a larger DNA construct. Often, such constructs allow stable expression of the RNAi in cells after introduction, e.g., by integration of the construct into the host genome. Thus, expression vectors that continually express iRNA in cells transfected with the vectors may be employed for this invention. For example, vectors that express small hairpin or stem-loop structure RNAs, or precursors to micro-RNA, which get processed in vivo into small RNAi molecules capable of carrying out gene-specific silencing (Brummelkamp et al., *Science* 296:550-553 (2002), and Paddison, et al., *Genes & Dev.* 16:948-958 (2002)) can be used. Post-transcriptional gene silencing by double-stranded RNA is discussed in further detail by Hammond et al. *Nature Rev Gen* 2: 110-119 (2001), Fire et al. *Nature* 391: 806-811 (1998) and Timmons and Fire *Nature* 395: 854 (1998).

Methods for selection and design of sequences that generate RNAi are well known in the art (e.g. Reynolds, 2004; see also U.S. Pat. Nos. 6,506,559; 6,511,824; and 6,489,127).

One of skill in the art will recognize that using technology based on specific nucleotide sequences (e.g., antisense or sense suppression technology), families of homologous genes can be suppressed with a single sense or antisense, discussed below, transcript. For instance, if a sense or antisense transcript is designed to have a sequence that is conserved among a family of genes, then multiple members of a gene family can be suppressed. Conversely, if the goal is to only suppress one member of a homologous gene family, then the sense or antisense transcript should be targeted to sequences with the most variation between family members.

The term "target RNA molecule", e.g., in this invention a target CAS1L RNA, refers to an RNA molecule to which an RNAi molecule is homologous or complementary.

One or more CAS1L genes can be inhibited using the same interfering RNA. For example, all of the CAS1L genes in a plant may be targeted by using an RNAi that is designed to a conserved region of the CAS1L gene. In other embodiments, individual CAS1L gene family members may be targeted by using an RNAi that is specific that CAS1L gene.

Antisense and Ribozyme Suppression

A reduction of CAS1L gene expression in a plant to reduce polysaccharide acetylation may be obtained by introducing into plants antisense constructs based on the CAS1L polynucleotide sequences. For antisense suppression, a CAS1L sequence is arranged in reverse orientation relative to the promoter sequence in the expression vector. The introduced sequence need not be a full length CAS1L cDNA or gene, and need not be identical to the CASL cDNA or a gene found in the plant variety to be transformed. Generally, however, where the introduced sequence is of shorter length, a higher degree of homology to the native CASL sequence is used to achieve for effective anti sense suppression. Preferably, the introduced antisense sequence in the vector will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous cspl gene. Suppression of endogenous CAS1L gene expression can also be achieved using a ribozyme. The production and use of ribozymes are disclosed in U.S. Pat. No. 4,987,071 to Cech and U.S. Pat. No. 5,543,508 to Haselhoff.

Mutagenesis

Alternatively, random mutagenesis approaches may be used to disrupt or "knock-out" the expression of a CAS1L gene using either chemical or insertional mutagenesis, or irradiation. One method of mutagenesis and mutant identification is known as TILLING (for targeting induced local lesions in genomes). In this method, mutations are induced in the seed of a plant of interest, for example, using EMS treatment. The resulting plants are grown and self-fertilized, and the progeny are assessed. For example, the plants may be assed using PCR to identify whether a mutated plant has a CAS1L mutation, e.g., that reduces expression of a CAS1L gene, or by evaluating whether the plant has reduced levels of acetate in a part of the plant that expressed the CAS1L gene. TILLING can identify mutations that may alter the expression of specific genes or the activity of proteins encoded by these genes (see Colbert et al (2001) *Plant Physiol* 126:480-484; McCallum et al (2000) *Nature Biotechnology* 18:455-457).

Another method for abolishing or decreasing the expression of a CAS1L gene is by insertion mutagenesis using the T-DNA of *Agrobacterium tumefaciens*. After generating the insertion mutants, the mutants can be screened to identify those containing the insertion in a CAS1L gene. Mutants containing a single mutation event at the desired gene may be crossed to generate homozygous plants for the mutation (Koncz et al. (1992) Methods in *Arabidopsis* Research. World Scientific).

Another method to disrupt a CAS1L gene is by use of the cre-lox system (for example, as described in U.S. Pat. No. 5,658,772).

Plants Having where Multiple CAS1L Genes are Inhibited

In some embodiments expression of two or more CAS1L genes is inhibited in a plant in accordance with the invention. As explained above, such plants can be generated by performing a molecular manipulation that targets all of the CAS1L gene family members in a plant, e.g., using an RNAi to a conserved region to inactivate all of the CAS1L genes. Such plants can also be obtained by breeding plants that each have individual mutations that inactivate different CAS1L genes to obtain progeny plants that are inactivated in all of the desired CAS1L genes. For example, to obtain a rice plant in which three CAS1L genes are inactivated, one of skill can target the genes using RNAi developed to a region that is conserved in all three of the rice CAS1L genes, or target the genes individually and breed the resulting mutant plants.

Expression of CAS1L Gene Inhibitors

Expression cassettes comprising polynucleotides that encodes CAS1L gene expression inhibitors, e.g., an antisense or siRNA, can be constructed using methods well known in the art. Constructs include regulatory elements, including promoters and other sequences for expression and selection of cells that express the construct. Typically, plant transformation vectors include one or more cloned plant coding sequences (genomic or cDNA) under the transcriptional control of 5' and 3' regulatory sequences and a dominant selectable marker. Such plant transformation vectors typically also contain a promoter (e.g., a regulatory region controlling inducible or constitutive, environmentally- or developmentally-regulated, or cell- or tissue-specific expression), a transcription initiation start site, an RNA processing signal (such as intron splice sites), a transcription termination site, and/or a polyadenylation signal.

Examples of constitutive plant promoters which may be useful for expressing the TF sequence include: the cauliflower mosaic virus (CaMV) 35S promoter, which confers constitutive, high-level expression in most plant tissues (see, e.g., Odel et al., (1985) *Nature* 313:810); the nopaline synthase promoter (An et al., (1988) *Plant Physiol.* 88:547); and the octopine synthase promoter (Fromm et al., (1989) *Plant Cell* 1:977).

Additional constitutive regulatory elements including those for efficient expression in monocots also are known in the art, for example, the pEmu promoter and promoters based on the rice Actin-1 5' region (Last et al., *Theor. Appl. Genet.* 81:581 (1991); Mcelroy et al., *Mol. Gen. Genet.* 231:150 (1991); Mcelroy et al., *Plant Cell* 2:163 (1990)). Chimeric regulatory elements, which combine elements from different genes, also can be useful for ectopically expressing a nucleic acid molecule encoding an IND1 polynucleotide (Comai et al., *Plant Mol. Biol.* 15:373 (1990)).

Other examples of constitutive promoters include the 1'- or 2'-promoter derived from T-DNA of *Agrobacterium tumafaciens* (see, e.g., Mengiste (1997) supra; O'Grady (1995) *Plant Mol. Biol.* 29:99-108); actin promoters, such as the *Arabidopsis* actin gene promoter (see, e.g., Huang (1997) *Plant Mol. Biol.* 1997 33:125-139); alcohol dehydrogenase (Adh) gene promoters (see, e.g., Millar (1996) *Plant Mol. Biol.* 31:897-904); ACT11 from *Arabidopsis* (Huang et al.

Plant Mol. Biol. 33:125-139 (1996)), Cat3 from *Arabidopsis* (GenBank No. U43147, Zhong et al., *Mol. Gen. Genet.* 251:196-203 (1996)), the gene encoding stearoyl-acyl carrier protein desaturase from *Brassica napus* (Genbank No. X74782, Solocombe et al. *Plant Physiol.* 104:1167-1176 (1994)), GPc1 from maize (GenBank No. X15596, Martinez et al. *J. Mol. Biol* 208:551-565 (1989)), Gpc2 from maize (GenBank No. U45855, Manjunath et al., *Plant Mol. Biol.* 33:97-112 (1997)), other transcription initiation regions from various plant genes known to those of skill. See also Holtorf *Plant Mol. Biol.* 29:637-646 (1995).

A variety of plant gene promoters that regulate gene expression in response to various environmental, hormonal, chemical, developmental signals, and in a tissue-active manner are known in the art. Examples of environmental conditions that may effect transcription by inducible promoters include anaerobic conditions, elevated temperature, drought, or the presence of light. Examples of environmental promoters include drought-inducible promoter of maize (Busk (1997) supra); the cold, drought, and high salt inducible promoter from potato (Kirch (1997) *Plant Mol. Biol.* 33:897 909). Plant promoters that are inducible upon exposure to plant hormones, such as auxins, may also be employed. For example, the invention can use the auxin response elements E1 promoter fragment (AuxREs) in the soybean (*Glycine max* L.) (Liu (1997) *Plant Physiol.* 115: 397 407); the auxin-responsive *Arabidopsis* GST6 promoter (also responsive to salicylic acid and hydrogen peroxide) (Chen (1996) *Plant J.* 10: 955 966); the auxin-inducible parC promoter from tobacco (Sakai (1996) 37:906 913); a plant biotin response element (Streit (1997) *Mol. Plant Microbe Interact.* 10:933 937); and, the promoter responsive to the stress hormone abscisic acid (Sheen (1996) *Science* 274:1900 1902).

Plant promoters which are inducible upon exposure to chemicals reagents that can be applied to the plant, such as herbicides or antibiotics, may also be used in vectors as described herein. For example, the maize In2 2 promoter, activated by benzenesulfonamide herbicide safeners, can be used; application of different herbicide safeners induces distinct gene expression patterns, including expression in the root, hydathodes, and the shoot apical meristem. Other promoters, e.g., a tetracycline inducible promoter; a salicylic acid responsive element promoter, promoters comprising copper-inducible regulatory elements; promoters comprising ecdysone inducible regulatory elements; heat shock inducible promoters, a nitrate-inducible promoter, or a light-inducible promoter may also be used.

In some embodiments, the plant promoter may direct expression of the polynucleotide of the invention in a specific tissue (tissue-specific promoters), such as a leaf or a stem. Tissue specific promoters are transcriptional control elements that are only active in particular cells or tissues at specific times during plant development, such as in vegetative tissues or reproductive tissues. Examples of tissue-specific promoters include promoters that initiate transcription primarily in certain tissues, such as vegetative tissues, e.g., roots or leaves, or reproductive tissues, such as fruit, ovules, seeds, pollen, pistils, flowers, or any embryonic tissue. Other examples are promoters that direct expression specifically to cells and tissues with secondary cell wall deposition, such as xylem and fibers.

Plant expression vectors may also include RNA processing signals that may be positioned within, upstream or downstream of the coding sequence. In addition, the expression vectors may include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Plant expression vectors routinely also include dominant selectable marker genes to allow for the ready selection of transformants. Such genes include those encoding antibiotic resistance genes (e.g., resistance to hygromycin, kanamycin, bleomycin, G418, streptomycin or spectinomycin), herbicide resistance genes (e.g., phosphinothricin acetyltransferase), and genes encoding positive selection enzymes (e.g. mannose isomerase).

Once an expression cassette comprising a polynucleotide encoding an inhibitor of the expression of a CAS1L gene, e.g., an antisense or siRNA, has been constructed, standard techniques may be used to introduce the polynucleotide into a plant in order to modify CAS1L activity and accordingly, the level of acetylation in the plant or plant part in which the CAS1L target nucleic acid is expressed. See protocols described in Ammirato et al. (1984) Handbook of Plant Cell Culture—Crop Species. Macmillan Publ. Co. Shimamoto et al. (1989) Nature 338:274-276; Fromm et al. (1990) Bio/Technology 8:833-839; and Vasil et al. (1990) Bio/Technology 8:429-434.

Transformation and regeneration of plants is known in the art, and the selection of the most appropriate transformation technique will be determined by the practitioner. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumeficiens* mediated transformation. Transformation means introducing a nucleotide sequence in a plant in a manner to cause stable or transient expression of the sequence. Examples of these methods in various plants include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Following transformation, plants are preferably selected using a dominant selectable marker incorporated into the transformation vector. Typically, such a marker will confer antibiotic or herbicide resistance on the transformed plants or the ability to grow on a specific substrate, and selection of transformants can be accomplished by exposing the plants to appropriate concentrations of the antibiotic, herbicide, or substrate.

Evaluation of Plants Engineered to Reduce CAS1L Expression.

After transformed plants are selected parts of the plants may be evaluated to determine the level of CAS1L gene expression in a part of the plant that expresses the CAS1L gene, e.g., by evaluating the level of RNA or protein, or determining the levels of acetate in the plants. These analyses can be performed using any number of methods known in the art.

In some embodiments, acetyl esters in plant cell wall material can be measured. For example, cell walls are prepared from plant material. Several methods are known. In the simplest method, the plant material is ground and extracted repeatedly with 96% and 70% ethanol. The resulting 'alcohol insoluble residue' is highly enriched in cell wall material. The sample is dried and resuspended in buffer at neutral pH. An aliquot of the sample is saponified by treatment with 0.1 M NaOH at 4° C. overnight or at room temperature for several hours. Following saponification, the sample is neutralized by adding 1 M HCl. Acetic acid in the saponified and neutralized sample can be determined in several different ways, e.g. by gas chromatography or HPLC on an appropriate column. A convenient method is to use an acetic acid determination kit, e.g., such as the kit by R-Biopharm, Germany, according to the manufacturers instructions. The principle of the kit is that acetate is enzymatically consumed in a series of reactions leading to the formation of NADPH, which can be determined spectrophotometrically at 340 nm. The kit allows for correction for interference in the determination.

The procedure above can be used to determine total acetyl esters in the alcohol insoluble residue. To determine acetate esters in specific polymers, the alcohol insoluble residue can be sequentially extracted and/or digested with specific enzymes. The extracts and digests can be analyzed by the methods described above or by mass spectrometry.

As appreciated by one in the art double, triple, or quadruple CAS1L mutant plants can be generated using techniques well known in the art, including breeding techniques as well as introducing mutations into a plant that already has a mutation in a CAS1L gene.

Plants that exhibit reduced CAS1L gene expression have at least 5% reduction in acetylation, e.g., as assessed by evaluating cell walls, typically at least 10% reduction in acetylation, or more often at least 15%, 20%, 30%, 40%, or 50% or more reduction in acetylation in comparison to a plant that has not been engineered to decrease expression of the CAS1L gene. In some embodiments, such a reduction in acetylation is observed when one CAS1L gene is reduced in expression in an engineered plant; in some embodiments, such a reduction in acetylation is observed when two CAS1L genes in the engineered plant have reduced expression, and in some embodiments, such a reduction in acetylation is observed when three or four CAS1L genes are engineered to decrease expression in the plant. As understood in the art, CAS1L-mediated reduction in acetylation may occur in one or more parts of the plants, e.g., acetylation may be reduced in a leaf and/or a stem.

Plants that exhibit reduced CAS1L gene expression can be used in a variety of methods. The plants selected for reduced acetate levels may further be evaluated to further confirm that the plants provide for improved yield. For example, plant material from the plants with reduced acetate content is ground or milled to defined particle size. The plant material can be compared to ground or milled plant material from normal plants that have not been engineered to reduce CAS1L gene expression.

The milled plant material is subjected to a saccharification procedure. Many different procedures are currently used experimentally, e.g. dilute acid treatment, steam explosion or ionic liquid treatments. As the beneficial effect of reduced acetate content will differ depending on the exact procedure used several different pretreatment methods can be evaluated. For example, a dilute acid treatment method can be used. The pretreated plant material is then subjected to enzymatic hydrolysis using a mixture of cell wall degrading enzymes.

Procedures for cell wall pretreatment and enzymatic digestion are well known to those skilled in the art. The yield or efficiency of the procedure can be readily determined by measuring the amount of reducing sugar released, using a standard method for sugar detection, e.g. the dinitrosalicylic acid method well known to those skilled in the art. Plants engineered in accordance with the invention provide a higher sugar yield.

CAS1L-inhibited plants may also be evaluated in comparison to non-engineered plants to test for the effect of acetates and acetate-derived compounds on subsequent fermentation. For example, hydrolyzed biomass is subjected to fermentation using an organism such as yeast or *E. coli* that can convert the biomass into compounds such as ethanol, butanol, alkanes, lipids, etc. In the simplest test, the yield of ethanol obtained with a given amount of starting plant material and a standard yeast fermentation can be determined. Yield can be determined not only with organisms that can ferment glucose, but also with organisms that have the ability to ferment pentoses and or other sugars derived from the biomass. In addition to determining the yield of product, e.g. ethanol, one can determine the growth rate of the organism. The plants of the invention that are engineered to reduce CAS1L activity and accordingly, to have reduced acetate, will exhibit a reduced inhibitory effect due to acetate and acetate-derived compounds in comparison to corresponding plants that have not be engineered to reduce CAS1L activity. The decreased inhibitory effect may result in higher final yields of a fermentation reaction, or in faster fermentation, or both.

Plants having reduced CAS1L activity can be used in a variety of reactions, including fermentation reactions. Such reactions are well known in the art. For example, fermentation reactions noted above, e.g., a yeast or bacterial fermentation reaction, may employ CAS1L mutants, to obtain ethanol, butanol, lipids, and the like. For example the plants may be used in industrial bioprocessing reactions that include fermentative bacteria, yeast, or filamentous fungi such as *Corynebacterium* sp., *Brevibacterium* sp., *Rhodococcus* sp., *Azotobacter* sp., *Citrobacter* sp., *Enterobacter* sp., *Clostridium* sp., *Klebsiella* sp., *Salmonella* sp., *Lactobacillus* sp., *Aspergillus* sp., *Saccharomyces* sp., *Zygosaccharomyces* sp., *Pichia* sp., *Kluyveromyces* sp., *Candida* sp., *Hansenula* sp., *Dunaliella* sp., *Debaryomyces* sp., *Mucor* sp., *Torulopsis* sp., *Methylobacteria* sp., *Bacillus* sp., *Escherichia* sp., *Pseudomonas* sp., *Serratia* sp., *Rhizobium* sp., and *Streptomyces* sp., *Zymomonas mobilis*, acetic acid bacteria, methylotrophic bacteria, *Propionibacterium, Acetobacter, Arthrobacter, Ralstonia, Gluconobacter, Propionibacterium*, and *Rhodococcus*.

Evaluation for Increased Resistance to Fungus

CAS1L mutant plants, e.g., plants that have mutations in CAS1L2, also exhibit increased resistance to certain fungi in comparison to plants that have wildtype CAS1L2 genes. CAS1L-inhibited plants may also be evaluated for susceptibility to infection, e.g., fungus infection. In some embodiments, such an assay may also be used to identify mutant CAS1L plants. An example of an assay to evaluate fungus resistance is provided in Example 3. CAS1L mutant plants may thus be more readily propagated, e.g., the plants could grown using reduced amounts of fungicide.

EXAMPLES

Example 1. Acetate Levels in CAS1L Mutant Plants

*Arabidopsis* mutants generated by random insertion of T-DNA were obtained from the *Arabidopsis* Biological Resource Center, Ohio, or constructed. Mutants where the T-DNA had been inserted in the coding region of the genes of interest, e.g., At3g06550, At2g34410, and At1g29890 were identified by searching the www website of arabidopsis.org. The website contains sequence information for flanking regions of T-DNA for all the mutants deposited. Mutant seeds were first screened to confirm the T-DNA insertion and identify homozygous plants. Seeds were germinated and leaf samples were used to prepare DNA and carry out PCR amplification using primers suggested by ABRC. The principle behind this PCR screening is that a primer complementary to the T-DNA together with a primer complementary to the plant genome near the insertion will yield a PCR product indicative of the insertion. Likewise, two primers complementary to the plant genome and placed on different sides of the site of insertion will only yield a PCR band if there is no insert, thus indicating the wild type allele. By using all three primers for PCR reactions, plants that were homozygous for the insertion could be identified by the presence of the insert-specific PCR product and the absence of the wild-type-specific PCR product. The homozygous individuals were grown to maturity and the seeds harvested. Homozygosity of the offspring was confirmed by PCR.

Acetate levels were initially evaluated in leaf samples from a small number of *Arabidopsis* plants that were generated. Cell walls were prepared from plant material. An aliquot of the sample was saponified using h 0.1 M NaOH. Following saponification, the sample was neutralized by adding 1 M HCl. Acetic acid in the saponified and neutralized sample was then determined with a colorimetric assay essentially according to Beutler (1984, in Methods of Enzymatic Analysis (Bergmeyer, H. U., ed.) 3rd ed., vol. VI, pp. 639-645, Verlag Chemie, Weinheim, Deerfield Beach/Florida, Basel).

The results are shown in FIG. 2. Plants in which CAS1L2 expression was decreased showed a statistically significant reduction in acetate levels. Plants that had inhibited CAS1L3 or CAS1L4 also exhibited a small reduction in acetate levels, although in the experiment depicted in FIG. 2 with the small number of plants, the reduction was not significant. A different CAS1L2 mutant plant (i.e., that had a different CAS1L2 mutation) also exhibited reduced acetate levels (data not shown).

An initial analysis also indicated that *Arabidopsis* plants in which CAS1L1 expression is inhibited exhibited reduced acetate levels in the stems.

Crosses of mutant CAS1L1, CAS1L2, CAS1L3, and CAS1L4 plants were also obtained in all combinations, i.e., all the single, double, triple, and quadruple mutants, were generated. The quadruple mutants and some of the triple mutant plants exhibited reduced plant growth.

Example 2. Enzymatic Digestion of Wild Type Arabadopsis and Mutant rwa2 to Determine the Effect of Acetylation on Saccharification Hydrolysis Kinetics This example demonstrates that plant material from CAS1L mutant plants is more easily saccharified into sugars.

Cell wall material was isolated as described (Harholt et al., *Plant Physiol.* 140:49-58, 2006). Rosette leaves from mature plants were ground to a powder in a ball mill and extracted with 96% and 70% ethanol.

Enzyme digestions were performed using Novozyme cellulase NS50013 and beta-glucosidase NS50010, with enzyme loadings of 10% wt enzyme/wt glucan and 1% wt enzyme/wt glucan, respectively. The percentage glucan was assumed to be 30% (dw) in all samples, and a 1% glucan loading was used for all reactions. All reactions were performed as duplicate technical replicates and two or three biological replicates.

Reactions were performed in 2 ml screwcap microcentrifuge tubes. Aproximately 10 mg of cell wall material was measured into the vials. A master mix containing 10% and 1% of NS50013 and NS50010 was prepared in 50 mM sodium acetate buffer, pH 4.8. Enzyme mixture was added to tubes on ice. Samples were then incubated for up to 72 hours in an ATR multitron shaker at 50 C and 1000 RPM.

At various time points, samples were removed from the shaker and centrifuged at 14000×g for 10 min. Supernatants were collected and diluted 1:100 for analysis. Monosaccharide concentrations were determined using High Performance Anion Exchange Chromatography with Pulsed Amperometric Detection (HPAEC-PAD) on a Dionex DX600 equipped with a Dionex Carbopac PA-20 analytical column (3×150 mm) and a Carbopac PA-20 guard column (3×30 mm) (Dionex, Sunnyvale, Calif.). Eluent flow rate was 0.4 mL min-1 and the temperature was 30° C. A gradient consisting of a 12 min elution with 14 mM NaOH followed by a 5 min ramp to 450 mM NaOH for 20 min, then a return to the original NaOH concentration of 14 mM for 10 min prior to the next injection. Product concentrations were determined using an external standard.

Figure 3:
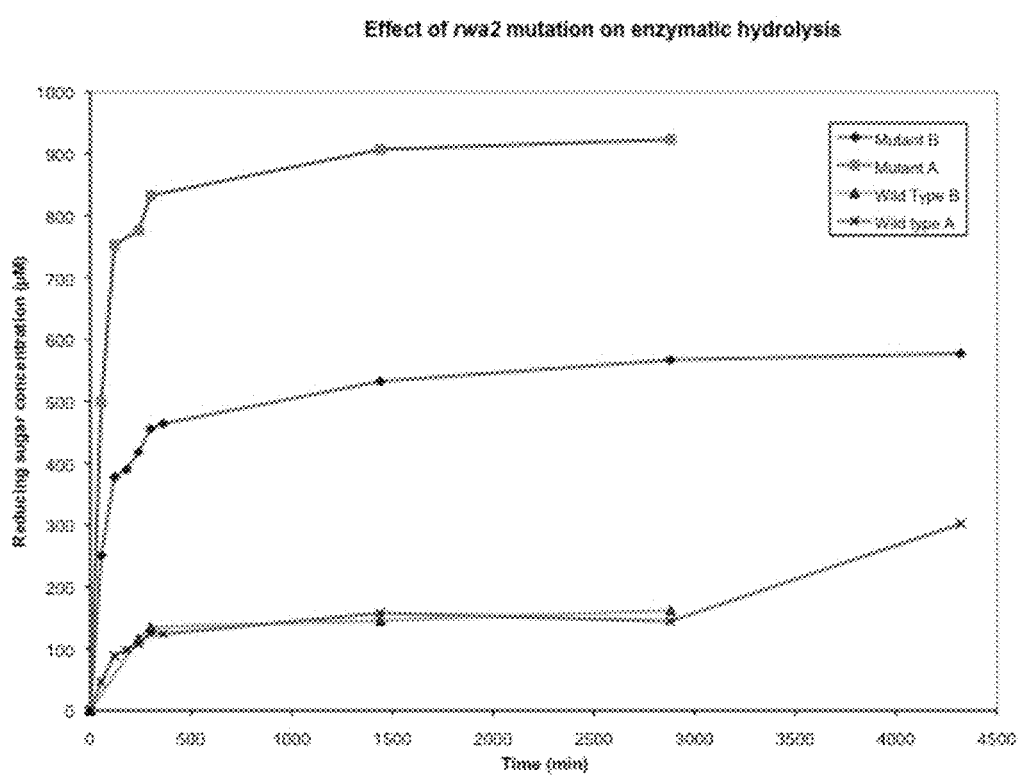
FIG. 3 provides data that illustrate the saccharification efficiency (determined as concentration of total monosaccharide released) as a function of time for cell wall material from wild type *arabidopsis* plants and rwa2-1. Rwa2-1 is an *Arabidopsis* plant with a mutated RWA2 gene, i.e., a mutated CAS1L2 gene.

In one experiment, a much higher amount of sugar was released from the leaf cell walls from the rwa2-1 mutant (see FIG. 3). Most of the released sugar is glucose, but xylose release showed the same difference with about 6-fold higher release from the rwa2 cell wall material. In a second experiment that was carried out is a similar way but with only a single time point of 24 hrs incubation, there was no significant difference between the mutant and the wildtype in total sugar release. However, the second experiment still showed a trend towards 3% increased xylose release from the mutant cell walls.

These experiments thus indicate that there is a benefit of reducing cell wall acetate on saccharification of biomass. The combined effect of a 20% reduction in hemicellulose acetylation on saccharification and on yeast fermentation has been simulated in a lignocellulose biorefinery model (Klein-Marchushamer et al., Techno-Economic Modeling of Cellulosic Biorefineries. Presented at DOE Genomic Science Awardee Workshop, Feb. 7-10, 2010, Crystal City, Va.). This simulation showed that an expected result would be a 10% decrease in cost per gallon of produced ethanol. The main effect is on the improved fermentation.

Example 3. RWA Mutant Plants have Decreased Susceptibility to Fungus

RWA muant plants also demonstrated increased resistant to fungus.

*Botrytis cinerea* IK2018 was isolated from strawberry fruit and obtained from Dr. Birgit Jensen, Dept. of Plant Biology and Biotechnology, University of Copenhagen, Denmark. *B. cinerea* was maintained on potato dextrose agar (Difco, USA). Spores were collected in 3 ml of 12 g/L potato dextrose broth (PDB; Difco, USA) by gentle rubbing and filtered through miracloth (Calbiochem/Merck, Germany) to remove mycelium. The number of spores was counted using a haemocytometer, and the suspension was adjusted to $5 \times 10^5$ conidiospores $ml^{-1}$ in PDB for infection of leaves.

Rosette leaves from 4-week-old soil-grown *Arabidopsis* plants (wild type Col-0 and the knock out mutants rwa2-1 and rwa2-3) were placed in Petri dishes containing 0.6% agar, with the petiole embedded in the medium. Inoculation was performed by placing 5 µl of a suspension of $5 \times 10^5$ conidiospores $ml^{-1}$ in 12 g $l^{-1}$ potato dextrose broth (PDB; Difco, Detroit, USA) on each side of the middle vein. The plates were incubated at 22° C. with a 12-h photoperiod. High humidity was maintained by covering the plates with a clear plastic lid. Lesion diameter in centimeters was obtained by hand analysis of high-resolution digital images of infected leaves using ImageJ (Abramoff et al., *Biophotonics International* 11:36-42, 2004). Included scale objects allowed standardization of measurements across images.

Figure 4:
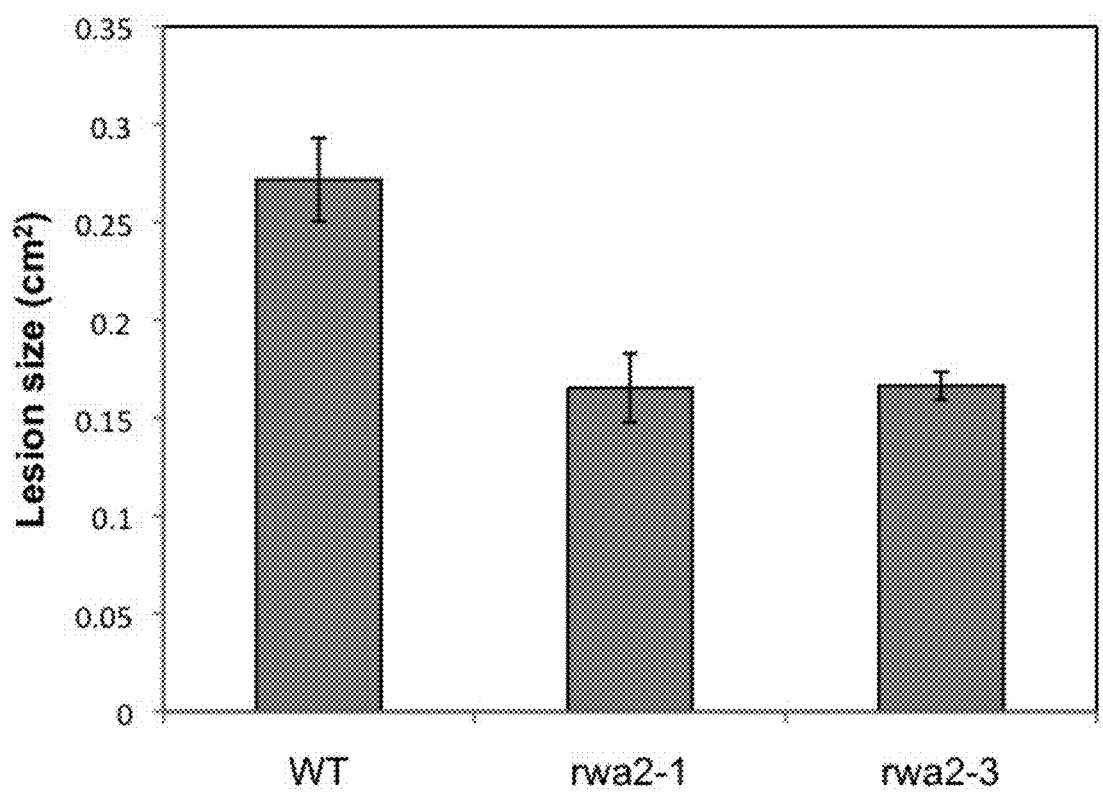
FIG. 4 shows the results of a *Botrytis cinerea* pathoassay 3 days post infection.

The results showed that rwa2 mutant plants with decreased wall acetylation exhibited a surprising tolerance to the necrotrophic fungal pathogen *Botrytis cinerea*. The experiment was carried out twice with essentially the same results. The result of one of the experiments is shown in FIG. 4.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, accession numbers, patents, and patent applications cited in this specification are herein incorporated by reference as if each was specifically and individually indicated to be incorporated by reference.

Examples of CAS1L1 (RWA) Polypeptide and Nucleic Acid Sequences

```
CAS1L1 Arabidopsis sequence (NP_568662.1) AT5G46340
                                                         (SEQ ID NO: 1)
   1  MVDPGPITPG QVSFLLGVIP IFVGWIYSEL LEYRKSWVPL KPHSDNNLVE LGDVAEKDDD

61  KADLLEGGLA RSPSVKFHNS SIRTNIIRFL SMEDSFLLEH RATLRAMSEF GAILIYFYIC

121  DRTELLGDST KNYNRDLFLF LYVLLIIVSA MTSLRKHNDK SPISGKSILY LNRHQTEEWK

181  GWMQVLFLMY HYFAAAEIYN AIRIFIAAYV WMTGFGNFSY YYVRKDFSVA RFAQMMWRLN

241  FFVAFCCIVL NNDYMLYYIC PMHTLFTLMV YGALGIFSKY NEIGSVMALK IFSCFLVVFL

301  LWEIPGAFEI FWGPLTFLLG YNDPAKPDLH RLHEWHFRSG LDRYIWIIGM IYAYYHPTVE

361  RWMEKLEDCE TKKRLSIKAA IVTITVLVGY VWYECIYKLD RTSYNMYHPY TSWIPITVYI

421  CLRNFTHQLR SVSLTLFAWL GKITLETYIS QFHIWLRSNM PDGQPKWLLS IIPGYPMLNF

481  MLTTAIYVLV SHRLFELTNT LKTVFVPTKD NKRLFSNFIA GIAIALPLYC FSFVLLQIHR

Cas1L2 protein sequence NP-001118592.1 AT3G06550
                                                         (SEQ ID NO: 2)
   1  MASSSPVTPG LMSVVFGIVP VIVAWLYSEY LHYAKYSVSA KTHSDVNLVE IAKDFVKEDD

61  KALLIEDGGG LQSASPRAKG PTTHSPLIRF VLLDESFLVE NRLTLRAIIE FAVLMVYFYI

121  CDRTDVFNSS KKSYNRDLFL FLYFLLIIVS AITSFTIHTD KSPFSGKAIM YLNRHQTEEW

181  KGWMQVLFLM YHYFAAAEYY NAIRVFIACY VWMTGFGNFS YYYIRKDFSL ARFAQMMWRL

241  NFLVIFSCIV LNNSYMLYYI CPMHTLFTLM VYGALGIMSK YNEMGSVIAA KFFACFVVVI

301  IVWEIPGVFE WIWSPFTLLM GYNDPAKPQL PLLHEWHFRS GLDRYIWIIG MLYAYYHPTV

361  ESWMDKLEEA EMKFRVAIKT SVALIALTVG YFWYEYIYKM DKLTYNKYHP YTSWIPITVY

421  ICLRNITQSF RGYSLTLLAW LGKITLETYI SQFHIWLRSG VPDGQPKLLL SLVPDYPLLN

481  FMLTTSIYVA ISYRLFELTN TLKTAFIPTK DDKRLVYNTI SALIICTCLY FFSFILITIP

541  QKLV

Cas1L2 protein sequence NP_001078116.1 AT3G06550
                                                         (SEQ ID NO: 5)
   1  MASSSPVTPG LMSVVFGIVP VIVAWLYSEY LHYAKYSVSA KTRHSDVNLV EIAKDFVKED

61  DKALLIEDGG GLQSASPRAK GPTTHSPLIR FVLLDESFLV ENRLTLRAII EFAVLMVYFY

121  ICDRTDVFNS SKKSYNRDLF LFLYFLLIIV SAITSFTIHT DKSPFSGKAI MYLNRHQTEE

181  WKGWMQVLFL MYHYFAAAEY YNAIRVFIAC YVWMTGFGNF SYYYIRKDFS LARFAQMMWR

241  LNFLVIFSCI VLNNSYMLYY ICPMHTLFTL MVYGALGIMS KYNEMGSVIA AKFFACFVVV

301  IIVWEIPGVF EWIWSPFTLL MGYNDPAKPQ LPLLHEWHFR SGLDRYIWII GMLYAYYHPT

361  VESWMDKLEE AEMKFRVAIK TSVALIALTV GYFWYEYIYK MDKLTYNKYH PYTSWIPITV

421  YICLRNITQS FRGYSLTLLA WLGKITLETY ISQFHIWLRS GVPDGQPKLL LSLVPDYPLL

481  NFMLTTSIYV AISYRLFELT NTLKTAFIPT KDDKRLVYNT ISALIICTCL YFFSFILITI

541  PQKLVSQNFI FLCGRKLFFP WYLSSLIC
```

-continued

Cas1L3 protein sequence NP_001031478.1 AT2G34410

(SEQ ID NO: 3)

```
  1  MADSQPITPG QVSFLLGVIP VFIAWIYSEF LEYKRSSLHS KVHSDNNLVE LGEVKNKEDE
 61  GVVLLEGGLP RSVSTKFYNS PIKTNLIRFL TLEDSFLIEN RATLRAMAEF GAILFYFYIS
121  DRTSLLGESK KNYNRDLFLF LYCLLIIVSA MTSLKKHNDK SPITGKSILY LNRHQTEEWK
181  GWMQVLFLMY HYFAAAEIYN AIRVFIAAYV WMTGFGNFSY YYIRKDFSLA RFTQMMWRLN
241  LFVAFSCIIL NNDYMLYYIC PMHTLFTLMV YGALGIFSRY NEIPSVMALK IASCFLVVIV
301  MWEIPGVFEI FWSPLTFLLG YTDPAKPELP LLHEWHFRSG LDRYIWIIGM IYAYFHPTVE
361  RWMEKLEECD AKRKMSIKTS IIAISSFVGY LWYEYIYKLD KVTYNKYHPY TSWIPITVYI
421  CLRNSTQQLR NFSMTLFAWL GKITLETYIS QFHIWLRSNV PNGQPKWLLC IIPEYPMLNF
481  MLVTAIYVLV SHRLFELTNT LKSVFIPTKD DKRLLHNVLA GAAISFCLYL TSLILLQIPH
```

Cas1L4 protein sequence NP174282.2 AT1G29890

(SEQ ID NO: 4)

```
  1  MFSSHNIFLT IGIVFIRRFL TLEDSFLLEN RATLRAMAEF GAILLYFYIC DRTSLIGQSQ
 61  KNYSRDLFLF LFCLLIIVSA MTSLKKHTDK SPITGKSILY LNRHQTEEWK GWMQVLFLMY
121  HYFAAVEFYN AIRVFIAGYV WMTGFGNFSY YYIRKDFSLA RFTQMMWRLN FFVAFCCIIL
181  NNDYMLYYIC PMHTLFTLMV YGALGIYSQY NEIASVMALK IASCFLVVIL MWEIPGVFEI
241  FWSPLAFLLG YTDPAKPDLP RLHEWHFRSG LDRYIWIIGM IYAYFHPTVE RWMEKLEECD
301  AKRRMSIKTS IIGISSFAGY LWYEYIYKLD KVTYNKYHPY TSWIPITVYI CLRNCTQQLR
361  RFSLTLFAWL GKITLETYIS QFHIWLRSSV PNGQPKLLLS IIPEYPMLNF MLTTAIYVLV
421  SVRLFELTNT LKSVFIPTKD DKRLLHNVIA MAAISFCLYI IGLILLLIPH
```

CAS1L1 (RWA1) nucleic acid sequence (coding sequence) NCBI Reference
Sequence: NM_124004.2

SEQ ID NO: 6

```
   1  atggtggatc ctggaccaat tactccgggc caggtatctt ttcttcttgg agtaatccca
  61  atatttgttg gttggatata ctcggagtta cttgagtaca gaaaatcttg ggttcccttg
 121  aaacctcact cggataataa tctagttgaa ttgggagacg tagcagagaa ggacgacgac
 181  aaagctgatc tgttggaggg aggtcttgcc cgatcaccat ctgtaaagtt tcataattca
 241  tctatcagaa caaacataat caggtttttg agtatggaag attcattttt gctggaacat
 301  cgagcaacct tgagagcaat gtcggaattt ggggcaatct aatatatttt ctatatctgt
 361  gaccgcacag aattgcttgg agattctacc aagaattaca accgcgacct tttcctttt
 421  ctctacgttc ttctcatcat agtatcagcc atgacatctc tcagaaaaca caatgacaag
 481  tcacccatat ctgggaagtc cattctttac cttaatcgcc accaaactga agaatggaaa
 541  ggatggatgc aggttttgtt cttaatgtat cactactttg ctgcggccga gatatacaac
 601  gcaatccgta tctttattgc tgcttatgtt tggatgactg ttttggaaa cttctcttac
 661  tactatgtca gaaaggattt ctctgttgca cgttttgcgc agatgatgtg gaggctgaac
 721  ttctttgtag cgttttgctg tattgttctc aacaacgact atatgttata ctacatctgc
 781  ccaatgcaca ctcttttcac cctaatggta tatggagctc tgggtatctt cagcaagtac
 841  aatgagatag gatcggtgat ggctctgaag atattttcat gcttcctcgt tgtcttttg
 901  ttgtgggaaa ttcctggagc ttttgaaata ttttggggtc ccttaacatt tttgctaggt
 961  tacaatgacc ctgccaagcc cgatcttcat cggctgcatg aatggcactt tagatcaggc
1021  cttgatcgct acatatggat catcggaatg atttatgcct attatcaccc aactgtagag
1081  agatggatgg agaagttaga ggactgtgaa acgaagaaaa gactatccat aaaggccgct
1141  attgttacta ttactgtgct tgttggctat gtgtggtatg aatgtatcta caagctggac
```

-continued

```
1201  aggaccagtt acaacatgta tcatccgtac acatcatgga tccccatcac tgtttacata 1261  tgccttcgga atttcaccca ccagcttcga agtgtctcat tgactctctt tgcgtggctt 1321  ggcaagatca ctttagagac ttacatttcc cagtttcata tatggctaag atcaaacatg 1381  cctgacgggc aaccaaaatg gcttctctct attattccgg gataccctat gctcaatttc 1441  atgctgacaa ctgctatata cgtccttgta tctcaccgtc tctttgaact aaccaacaca 1501  ctcaagacgg ttttcgtacc cacaaaagac aacaagcgac tcttctctaa cttcatagct 1561  gggattgcca tcgctcttcc actctattgc ttctcattcg ttcttcttca gattcatcgt 1621  tag
```

CAS1L2 (RWA2) nucleic acid sequence (coding sequence) NCBI Reference
Sequence: NM_001125120.1

SEQ ID NO: 7

```
  1  atggcgagtt caagccctgt tacacctggg ctaatgtcgg tggtgttcgg gattgtgccg 61  gtgatcgtgg cttggctata ctctgagtat ctgcactatg ctaaatactc ggtctccgcc 121  aaaacgcact ctgatgtcaa tttggtggaa attgcgaaag atttttgttaa agaagatgac 181  aaagctcttt taatagaaga tggaggtggt ctccaatcag cttctcctag agccaaaggc 241  ccgaccacac attctcctct catcaggttt gtcctcttgg atgagtcgtt cttggttgag 301  aacaggctga ctttaagggc aataattgag tttgcagtac ttatggtata cttttacata 361  tgtgaccgca cagatgtctt caattcatca aagaagagtt acaaccggga tctctttctg 421  ttcctttact tccttctcat catcgtttca gcgataactt cattcacgat acatactgat 481  aaatcaccat tcagcggaaa agccatcatg tacttgaata ggcatcaaac cgaggagtgg 541  aaaggctgga tgcaggtcct tttcttgatg taccactact ttgctgctgc agagtactat 601  aatgcgatcc gtgttttcat tgcttgctat gtatggatga ctggatttgg gaattttttct 661  tattattaca ttcgcaagga ctttagcctt gcaaggtttg cacagatgat gtggcggcta 721  aatttcctgg tcatattctc ctgcatcgtc ctcaacaaca gttacatgct atactacatc 781  tgcccaatgc acactctgtt tactctaatg gtctatgggg cacttggtat tatgagcaag 841  tataatgaga tgggttcagt catagctgcc aaatttttg cctgcttcgt tgttgttatc 901  atcgtttggg aaattcctgg cgttttgaa tggatttgga gtccatttac actcctaatg 961  ggttacaatg atcccgcaaa acctcagctt cccctcttgc atgagtggca tttccgctct 1021  ggacttgatc ggtacatatg gataatcggg atgctatatg catactacca cccaactgtt 1081  gaaagttgga tggataaact ggaggaagct gagatgaaat tcagggtggc tatcaaaaca 1141  tctgtggcac tgatagcact aacggtggga tattttttggt acgagtatat atacaagatg 1201  gacaagttaa cttacaacaa atatcatcct tacacctctt ggattccaat aactgtttat 1261  atctgtctcc ggaacatcac ccagtctttc cgcggctaca gtttgaccct tctggcgtgg 1321  cttggaaaga taacactgga gacatatatc tcccagtttc atatatggct cagatctgga 1381  gttcctgatg tcaacccaa attactacta tctcttgtcc cggattaccc attgttgaac 1441  ttcatgctca ctacttcgat ttacgtcgct atctcttata ggctctttga gcttaccaac 1501  actttgaaaa cagccttcat accaaccaag gacgacaaac gccttgtcta aacacgatc 1561  tcagcactca taatctgcac ttgtctctac ttttttctcat ttattcttat cacaattccc 1621  caaaaactgg tgtga
```

CAS1L2 (RWA2) nucleic acid sequence (coding sequence) NCBI Reference
Sequence: NM_001084647.4

SEQ ID NO: 8

```
  1  atggcgagtt caagccctgt tacacctggg ctaatgtcgg tggtgttcgg gattgtgccg 61  gtgatcgtgg cttggctata ctctgagtat ctgcactatg ctaaatactc ggtctccgcc
```

```
 121   aaaactaggc actctgatgt caatttggtg gaaattgcga agatttttgt taaagaagat
 181   gacaaagctc ttttaataga agatggaggt ggtctccaat cagcttctcc tagagccaaa
 241   ggcccgacca cacattctcc tctcatcagg tttgtcctct tggatgagtc gttcttggtt
 301   gagaacaggc tgactttaag ggcaataatt gagtttgcag tacttatggt atacttttac
 361   atatgtgacc gcacagatgt cttcaattca tcaaagaaga gttacaaccg ggatctcttt
 421   ctgttccttt acttccttct catcatcgtt tcagcgataa cttcattcac gatacatact
 481   gataaatcac cattcagcgg aaaagccatc atgtacttga ataggcatca aaccgaggag
 541   tggaaaggct ggatgcaggt ccttttcttg atgtaccact actttgctgc tgcagagtac
 601   tataatgcga tccgtgtttt cattgcttgc tatgtatgga tgactggatt tgggaattt t
 661   tcttattatt acattcgcaa ggactttagc cttgcaaggt ttgcacagat gatgtggcgg
 721   ctaaatttcc tggtcatatt ctcctgcatc gtcctcaaca acagttacat gctatactac
 781   atctgcccaa tgcacactct gtttactcta atggtctatg ggcacttgg tattatgagc
 841   aagtataatg agatgggttc agtcatagct gccaaatttt ttgcctgctt cgttgttgtt
 901   atcatcgttt gggaaattcc tggcgttttt gaatggattt ggagtccatt tacactccta
 961   atgggttaca atgatcccgc aaaacctcag cttccctct tgcatgagtg gcatttccgc
1021   tctggacttg atcggtacat atggataatc gggatgctat atgcatacta ccacccaact
1081   gttgaaagtt ggatggataa actggaggaa gctgagatga aattcagggt ggctatcaaa
1141   acatctgtgg cactgatagc actaacggtg ggatatttt ggtacgagta tatatacaag
1201   atggacaagt taacttacaa caaatatcat ccttacacct cttggattcc aataactgtt
1261   tatatctgtc tccggaacat cacccagtct ttccgcggct acagtttgac ccttctggcg
1321   tggcttggaa agataacact ggagacatat atctcccagt ttcatatatg gctcagatct
1381   ggagttcctg atggtcaacc caaattacta ctatctcttg tccggatta cccattgttg
1441   aacttcatgc tcactacttc gatttacgtc gctatctctt ataggctctt tgagcttacc
1501   aacactttga aaacagcctt cataccaacc aaggacgaca aacgccttgt ctacaacacg
1561   atctcagcac tcataatctg cacttgtctc tactttttct catttattct tatcacaatt
1621   ccccaaaaac tggtaagtca aaattttatc tttttgtgtg ggagaaagct tttttttccc
1681   tggtacttga gttcattgat atgttag
```

CAS1L3 (RWA3) nucleic acid sequence (coding sequence)

SEQ ID NO: 9
```
   1   atggcggatt ctcagccaat cacgcctggt caggtttcgt ttctactcgg agtcattcct
  61   gtcttcatag catggattta ctcagagttt ctagagtata agaggtcttc attgcactct
 121   aaagttcatt cagataataa tttggttgaa cttggtgagg taaaaaacaa ggaagatgaa
 181   ggagtagttt tacttgaagg aggtcttcca agatcagtct ctacaaagtt ttataactca
 241   cctatcaaaa caaacttgat tagatttctg acgctggaag actctttctt gattgaaaat
 301   cgagcaacct tgagagcgat ggctgagttt ggggctattc ttttttactt ttatattagt
 361   gatcgaacaa gcttgcttgg agagtctaaa aagaattaca acagagatct tttcctcttt
 421   ctctactgtc ttctcatcat agtttcagcc atgacatcct tgaagaaaca caatgacaaa
 481   tcacctataa caggaaaatc cattctctat cttaatcgtc accagactga agagtggaag
 541   ggatggatgc aggttctatt tcttatgtat cattactttg ctgcggctga gatatataat
 601   gcaatcaggg ttttcattgc tgcctacgtc tggatgactg ggtttgggaa cttctcttat
 661   tactatatca gaaaggattt ctccctagca cgattactc agatgatgtg gcgtcttaac
```

-continued

```
 721   ttatttgtgg cgtttagctg cattattctc aataatgatt atatgctgta ctacatctgt 781   ccaatgcaca ctctgttcac tcttatggtg tatggagccc ttggtatctt cagtcgatat 841   aacgaaatac catcagtaat ggctttgaag attgcttcat gctttctcgt ggttatcgtg 901   atgtgggaga ttcctggcgt ttttgagatt ttctggagtc ctttaacatt cttactggga 961   tacactgatc cagctaaacc agaactacca cttttacatg aatggcactt cagatcagga 1021   cttgaccgct acatatggat cattggaatg atatatgcct atttccatcc cactgtagag 1081   agatggatgg agaaattgga ggagtgtgat gccaagagaa agatgtcaat aaagacaagc 1141   ataattgcaa tttcctcatt tgttggttac ctatggtatg aatacatata caagcttgac 1201   aaggttacat acaacaaata tcatccctac acatcgtgga ttccaataac cgtctacatc 1261   tgtctgcgaa attctacaca acagctgcgt aatttctcca tgacactatt tgcgtggctc 1321   ggcaagatta ctctggaaac ctatatttct cagtttcaca tctggttaag atcgaatgtg 1381   ccaaatggac agcctaagtg gctattatgc attattccag aatacccaat gctcaacttc 1441   atgctcgtca cggccatcta tgtcttggtg tcccaccgac ttttcgagct tacaaacacg 1501   ttaaagtctg ttttcatacc aacaaaagac gacaagaggc tgctccacaa tgttctcgct 1561   ggagctgcca tctcgttctg tttatattta acatctctca ttcttctcca gatcccacac 1621   taa
```

CAS1L4 (RWA4) nucleic acid sequence (coding sequence) NCBI Reference Sequence: NM_102729.2

SEQ ID NO: 10

```
   1   atgttctcta gccataatat tttcttaacc attggcattg tgtttattcg taggtttctg 61   actttggaag actctttctt gcttgaaaac cgagcaacct tgagagcaat ggctgagttt 121   ggagcaattc ttttatattt ttatatttgt gatcgaacta gcttgatcgg gcagtctcaa 181   aagaattaca gccgagacct ttttctcttt ctcttctgtc ttctcatcat agtgtcagct 241   atgacgtcct tgaagaaaca cactgacaag tcaccaataa caggaaagtc cattctgtat 301   ctcaatcgtc accagactga agaatggaaa gggtggatgc aggttctatt tctgatgtat 361   cattattttg cggcagttga gttttacaat gcaatcaggg tcttcatcgc tggctatgtg 421   tggatgaccg gttttgggaa cttctcttat tactatatcc gaaaggattt ctcccttgca 481   cgattcactc agatgatgtg gcggcttaac ttttttgtgg cgttttgttg cattattctc 541   aacaatgact atatgctgta ctacatctgt ccaatgcaca ctctattcac gctgatggtc 601   tatggagccc ttggtatttta cagtcagtat aacgaaatag catcagtgat ggctctgaag 661   attgcttcat gctttctcgt ggttatcctt atgtgggaga ttcctggagt ttttgagatt 721   ttctggagtc ctctggcatt cttactgggg tacacagatc cagctaaacc agaccttcca 781   cgtctacacg aatggcattt cagatctgga cttgatcgct acatatggat catcggcatg 841   atatatgcat attttcatcc cactgtagaa agatggatgg agaaattgga ggagtgtgat 901   gctaagagaa ggatgtcaat caagacaagc ataataggaa tttcttcatt cgctggttac 961   ctttggtatg aatacatcta caagctggac aaggttacgt acaacaaata tcatccctac 1021   acatcttgga ttccaataac tgtctacatc tgtctgcgaa attgcaccca acagctacgg 1081   agattttccc tgacactctt tgcgtggctg ggcaagataa ctctcgagac ctacatttca 1141   cagtttcaca tctggttaag atcgagtgtg ccaaatgggc agccaaagtt gctattatca 1201   atcatcccag aatacccaat gctcaacttc atgctcacca cggccatcta cgtcttggta 1261   tctgttcgac ttttcgagct aaccaataca ttaaaatcag ttttcatacc cacgaaagac
```

```
1321  gacaaacggc tgctccacaa cgtgattgct atggctgcga tatcattttg tttatatatt 1381  atcggtctta ttcttctctt gatcccacat taa
```

What is claimed is:

1. A method of engineering a plant to reduce acetylation in the stem of a plant; wherein the plant is *Arabidopsis*, poplar, or rice, the method comprising:
   - genetically modifying the plant to inhibit expression of all endogenous RWA genes in fiber tissue of the plant, wherein the step of inhibiting expression of each of the endogenous RWA genes in the fiber tissue of the plant comprises introducing one or more expression cassettes into the plant, said one or more expression cassettes encoding one or more polynucleotides that hybridize to the target endogenous RWA nucleic acids, or complements thereof, and inhibit expression of the endogenous RWA genes, expression of which said one or more polynucleotides is driven by a fiber-specific promoter, and
   - wherein each endogenous RWA gene encodes an RWA polypeptide comprising:
     - (i) an amino acid sequence YLNRHQTEEWKGWMQVXFLMYHYFXAXEXYNAIRXFIAXYVWMTGFGNFSY YYXXKDFSXXRFXQMMWRLNXXVXXXCXXLXNXYXLYYICPMHTLFTXMVY (SEQ ID NO:12), wherein X at position 17 is L or I; X at position 25 is A or N, X at position 27 is A, T, or V; X at position 29 is Y, I or F; X at position 35 is I, V, L, or M; X at position 39 is A, G, C, or S; X at position 54 is I or V, X at position 55 is R or K; X at position 60 is V, L, or I; X at position 61 is A; X at position 64 is S, A or T; X at position 72 is F or L, X at position 73 is F or L, X at position 75 is A, T, L, or I; X at position 76 is F or V, X at position 77 is C or S; X at position 79 is I or V, X at position 80 is I or V; X at position 82 is N or D; X at position 84 is D or S, X at position 86 is M or T; and X at position 99 is L or V; and
     - (ii) an amino acid sequence comprising SEQ ID NO:13; and
   - evaluating acetylation in the stem of the plant and selecting a plant that has reduced acetylation in the stem compared to wild-type.

2. The method of claim 1, wherein X at position 25 is A, X at position 35 is I, V, or M; X at position 55 is R; X at position 60 is V or L; X at position 75 is A, L, or I; and X at position 86 is M.

3. A plant engineered by the method of claim 1.

4. Bulk harvested material comprising the plant of claim 3.

5. Bulk harvested material comprising the plant of claim 3, wherein the material is present in a fermentation reaction.

6. The method of claim 1, wherein the plant is a *Populus trichcarpa* plant.

\* \* \* \* \*